US011877994B2

(12) United States Patent
Mühler et al.

(10) Patent No.: US 11,877,994 B2
(45) Date of Patent: Jan. 23, 2024

(54) TREATMENT OF MULTIPLE SCLEROSIS COMPRISING DHODH INHIBITORS

(71) Applicant: Immunic AG, Gräfelfing (DE)

(72) Inventors: Andreas Mühler, Munich (DE); Hella Kohlhof, Munich (DE); Daniel Vitt, Germering (DE)

(73) Assignee: IMMUNIC AG, Grafelfing (DE)

(*) Notice: Subject to any disclaimer, the term of this patent is extended or adjusted under 35 U.S.C. 154(b) by 57 days.

(21) Appl. No.: 17/391,442

(22) Filed: Aug. 2, 2021

(65) Prior Publication Data
US 2023/0051911 A1 Feb. 16, 2023

(51) Int. Cl.
*A61K 31/192* (2006.01)
*A61K 9/00* (2006.01)
(Continued)

(52) U.S. Cl.
CPC .......... *A61K 31/192* (2013.01); *A61K 9/0053* (2013.01); *A61K 31/136* (2013.01);
(Continued)

(58) Field of Classification Search
CPC .. A61P 25/28; A61P 29/00; A61P 1/00; A61P 1/04; A61P 11/02; A61P 11/06; A61P 17/00; A61P 17/02; A61P 17/06; A61P 19/02; A61P 19/04; A61P 25/00; A61P 27/02; A61P 31/04; A61P 31/12; A61P 31/14; A61P 33/00; A61P 33/02; A61P 35/00; A61P 37/00; A61P 37/06; A61P 19/06; Y02A 50/30; C07B 2200/13; C07C 233/60; C07C 233/59; C07C 255/60; C07C 2601/10; C07D 307/30; C07D 333/38; C07D 333/58; A61K 31/196; A61K 9/0053; A61K 2300/00; A61K 31/706; A61K 45/06; A61K 9/20; A61K 31/192; A61K 31/136; A61K 31/137; A61K 31/225;
(Continued)

(56) References Cited

U.S. PATENT DOCUMENTS

2013/0197080 A1* 8/2013 Rocklin ................ A61K 31/277
514/521
2020/0360324 A1* 11/2020 Gröppel ............... A61K 31/196
2021/0017125 A1* 1/2021 Vitt ......................... C07C 233/60

FOREIGN PATENT DOCUMENTS

| CA | 2930429 | 5/2015 |
| WO | 2012001148 A1 | 1/2012 |

OTHER PUBLICATIONS

Muehler et al. (Multiple sclerosis and related Disorders, 473 (Aug. 2020) 102129, pp. 1-8 ) (Year: 2020).*
(Continued)

*Primary Examiner* — Savitha M Rao
(74) *Attorney, Agent, or Firm* — FINNEGAN, HENDERSON, FARABOW, GARRETT & DUNNER, LLP

(57) ABSTRACT

Methods of treating or ameliorating multiple sclerosis by the dihydroorotate dehydrogenase (DHODH) inhibitor vidofludimus or a pharmaceutically acceptable salt and/or a solvate, in particular a hydrate, thereof or a solvate, in particular a hydrate, of a pharmaceutically acceptable salt thereof, by administering to a human patient a therapeutically effective amount of the DHODH inhibitor, more specifically a daily dose of about 10 mg to about 45 mg.

18 Claims, 5 Drawing Sheets

(51) Int. Cl.
    *A61K 38/21*    (2006.01)
    *A61K 31/785*    (2006.01)
    *A61K 31/136*    (2006.01)
    *A61P 25/28*    (2006.01)
    *A61K 31/225*    (2006.01)
    *A61K 31/4704*    (2006.01)
    *A61K 31/397*    (2006.01)
    *A61K 31/137*    (2006.01)
    *A61K 39/395*    (2006.01)

(52) U.S. Cl.
    CPC .......... *A61K 31/137* (2013.01); *A61K 31/225* (2013.01); *A61K 31/397* (2013.01); *A61K 31/4704* (2013.01); *A61K 31/785* (2013.01); *A61K 38/215* (2013.01); *A61K 39/3955* (2013.01); *A61P 25/28* (2018.01)

(58) Field of Classification Search
    CPC .............. A61K 31/397; A61K 31/4704; A61K 31/785; A61K 38/215; A61K 39/3955
    See application file for complete search history.

(56) References Cited

OTHER PUBLICATIONS

Herrlinger KR et al, "Efficacy, safety and tolerability of vidofludimus in patients with inflammatory bowel disease: The Entrance study", Journal of Crohn's and Colitis, 2013, 7, 636-643. DOI: 10.1016/J.CROHNS.2012.09.016.

Musuamba FT et al Advanced Methods for Dose and Regimen Finding During Drug Development: Summary of the EMA/EFPIA Workshop on Dose Finding (London Dec. 4-5, 2014).

Fitzpatrick LR et al, "Vidofludimus Inhibits Colonic Interleukin-17 and Improves Hapten-Induced Colitis in Rats by a Unique Dual Mode of Action", The Journal of Pharmacology and Experimental Therapeutics, 2012, 342, 850-860, published online Aug. 14, 2012. DOI: 10.1124/jpet.112.192203.

Rusai K et al "Immunosuppression With 4SC-101, a Novel Inhibitor of Dihydroorotate Dehydrogenase, in a Rat Model of Renal Transplantation", Transplantation, 2012, 93, 1101-1107, published Jun. 15, 2012. DOI: 10.1097/TP.0b013e31824fd861.

Catana C et al, "Contribution of the IL-17/IL-23 axis to the pathogenesis of inflammatory bowel disease", World J Gastroenterol, 2015, 21(19), 5823-5830, published online May 21, 2015. DOI: 10.3748/wjg.v21.i19.5823.

Hanke T et al, "Small molecules with anti-inflammatory properties in clinical development", Pharmacology & Therapeutics, 2016, 157, 163-187, published online Nov. 26, 2015. DOI: 10.1016/j.pharmthera.2015.11.011.

Fitzpatrick LR, "Inhibition of IL-17 as a Pharmacological Approach for IBD", International Reviews of Immunology, 2013, 32, 544-555, published online: Jul. 25, 2013, DOI: 10.3109/08830185.2013.821118.

Gómez-Gómez GJ et al, "Current stage in inflammatory bowel disease: What is next?", World J Gastroenterol 2015, 21(40), 11282-11303, published online: Oct. 28, 2015. DOI: 10.3748/wjg.v21.i40.11282.

Fitzpatrick LR et al, "Vidofludimus Inhibits Colonic IL-17 and Improves Hapten-Induced Colitis in Rats by a Unique Dual Mode of Action", conference presentation at Digestive Disease Week, San Diego in May 19-22, 2012.

Fitzpatrick LR et al, "Vidofludimus Inhibits Colonic IL-17 and Improves Hapten-Induced Colitis in Rats by a Unique Dual Mode of Action", Gastroenterology 2012, 142(5), Supplement 1, S-84, published May 2012. DOI: 10.1016/S0016-5085(12)60317-5.

Hamm S et al, "Vidofludimus induces p53-mediated apoptosis in activated T cells and inhibits IL-17A and IL-17F expression decoupled from lymphocyte proliferation", poster presentation at Digestive Disease Week, San Diego in May 19-22, 2012, Abstract No. Tu1875.

Hamm S et al, "Vidofludimus induces p53-mediated apoptosis in activated T cells and inhibits IL-17A and IL-17F expression decoupled from lymphocyte proliferation", poster presentation at 7th Congress of ECCO—IBD, Feb. 17, 2012, Poster No. P013.

Fitzpatrick LR et al, "Vidofludimus Inhibits IL-17 and Improves Hapten-Induced Colitis in Young Rats by a Unique Dual Mode of Action", poster presentation at 7th Congress of ECCO—Inflammatory Bowel Disease Feb. 17, 2012, Barcelona, Spain, Poster No. P012.

Kulkarni OP et al, "4SC-101, A Novel Small Molecule Dihydroorotate Dehydrogenase Inhibitor, Suppresses Systemic Lupus Erythematosus in MRL-(Fas)lpr Mice", The American Journal of Pathology, 2010, 176(6), 2840-2847, published online: Apr. 22, 2010. DOI: 10.2353/ajpath.2010.091227.

Sierakowski S et al "Efficacy, Safety and Pharmacokinetics of Vidofludimus, a Novel Oral Immunomodulator, in Patients with Active Rheumatoid Arthritis on Methotrexate Background Therapy: The Component Study", poster presentation at American College of Rheumatology Nov. 4-10, 2011, Chicago, IL (USA), Abstract #18848.

Kulkarni O et al, "Vidofludimus shows a superior profile compared to cyclophosphamide and MMF in an experimental systemic lupus erythematosus model", poster presentation at European League Against Rheumatism (EULAR) Congress, London, United Kingdom, May 25-28, 2011.

Fitzpatrick LR et al, "Inhibition of IL-17 Release by the Novel Anti-Inflammatory Drug Vidofludimus Involves Attenuation of STAT3 and NF-kappa B Signaling Pathways in Murine Splenocytes and Hapten-Induced Colitis", poster presentation at Digestive Disease Week 2011, Chicago, May 7-11, Abstract No. Tu1800.

Herrlinger KR et al, "Efficacy, Safety and Tolerability of Vidofludimus in Patients with Inflammatory Bowel Disease: the Entrance Study", poster presentation at 6th Congress of ECCO—Inflammatory Bowel Disease Feb. 25, 2011, Dublin, Ireland, Poster No. P209.

Fitzpatrick LR et al, "4SC-101, a Novel Immunosuppressive Drug, Inhibits IL-17 and Attenuates Colitis in Two Murine Models of Inflammatory Bowel Disease" Inflamm Bowel Dis, 2011, 16(10), 1763-1777, published online: Mar. 22, 2010. DOI: 10.1002/ibd.21264.

Fitzpatrick LR et al, "A Novel Immunosuppressive Drug (4SC-101) Improves TNBS-Induced Colitis in Mice", poster presentation at Digestive Disease Week 2011, Chicago, May 7-11, Abstract No. M1658.

Leban J et al, "SAR, species specificity, and cellular activity of cyclopentene dicarboxylic acid amides as DHODH inhibitors", Bioorg Med Chem Lett, 2005, 15(21), 4854-4857, published online Sep. 6, 2005. DOI: 10.1016/j.bmcl.2005.07.053.

Leban J et al, "Discovery of a novel series of DHODH inhibitors by a docking procedure and QSAR refinement", Bioorg Med Chem Lett. 2004, 14(1), 55-58, published online Dec. 2, 2003. DOI: 10.1016/j.bmcl.2003.10.021.

Baumgartner R et al, "Dual Binding Mode of a Novel Series of DHODH Inhibitors", J. Med. Chem. 2006, 49, 1239-1247, published online Jan. 26, 2006. DOI: 10.1021/jm0506975.

Fitzpatrick LR et al, "A Novel Immunosuppressive Drug (4SC-101) Improves TNBS-Induced Colitis in Mice", poster presentation at Digestive Disease Week 2009, Chicago, USA, May 28, 2009.

Strobl S et al, "Vidofludimus, a New IL-17 and DHODH Inhibitor for Treatment of Inflammatory and Autoimmune Diseases", poster presentation at 14th International Symposium on Purine and Pyrimidine Metabolism in Man, Tokyo, Japan, Feb. 8-21, 2011.

Herrlinger KR et al, "Efficacy, Safety and Tolerability of Vidofludimus in Patients with Inflammatory Bowel Disease: the Entrance Study", Digestive Disease Week, May 7-10, 2011, Chicago, IL (USA), Abstract #1034088.

Fitzpatrick LR et al, "Novel Pharmacological Approaches for Inflammatory Bowel Disease: Targeting Key Intracellular Pathways and the IL-23/IL-17 Axis", Int J Inflam, 2012, 389404. published online Mar. 15, 2012. DOI: 10.1155/2012/389404.

(56) References Cited

OTHER PUBLICATIONS

"Immunic, Inc. Announces 200 Patients Enrolled in Its Phase 2 CALVID-1 Trial of IMU-838 for the Treatment of Moderate COVID-19, Allowing for Main Phase 2 Efficacy Analysis to Proceed", press release, Immunic Inc, Nov. 2, 2020.
"Immunic, Inc. Announces Results From Interim Safety Analysis and Recruitment Update From Its Ongoing Phase 2 CALVID-1 Trial of IMU838 in Patients With Moderate COVID-19", press release, Immunic Inc, Sep. 28, 2020.
"Immunic, Inc. Publishes Full Unblinded Clinical Data From Phase 2 EMPHASIS Trial of IMU-838 in Patients With Relapsing-Remitting Multiple Sclerosis and Announces Poster Presentation at the MSVirtual2020", press release, Immunic Inc, Sep. 11, 2020.
"Immunic Therapeutics—IMU-838 Phase 2 Data EMPhASIS Trial in RRMS", presentation from Sep. 11, 2020.
"Immunic, Inc. Reports Positive Top-line Data from Phase 2 EMPhASIS Trial of IMU-838 in Patients with Relapsing-Remitting Multiple Sclerosis", press release, Immunic Inc, Aug. 2, 2020.
"Immunic Therapeutics IMU-838 Phase 2 Top-Line Data EMPhASIS Trial in RRMS", presentation from Aug. 3, 2020.
"Immunic Therapeutics Inaugural R&D Day", presentation from Immunic Virtual R&D Day, May 19, 2020.
Fox R, "Multiple Sclerosis Treatment Landscape and Unmet Needs", presentation from Immunic Virtual R&D Day, May 19, 2020.
"Developing Selective Oral DHODH Inhibitor IMU-838 as COVID-19 Therapy", presentation from Apr. 22, 2020.
Muehler A et al, "The DHODH Inhibitor IMU-838/Vidofludimus Calcium Shows a Superior Compound Profile as Compared to the Approved DHODH Inhibitor, Teriflunomide", poster presentation at the Congress of the European Committee for Treatment and Research in Multiple Sclerosis 2019, Sep. 11, 2019.
Kohlhof H, "IMU-838 in Clinical Phase 2—New Selective Oral Treatment for IBD", presentation at GI Inflammatory Diseases Summit (GIIDS) in Boston, US, Jun. 24, 2019.
Muehler A et al, "Vidofludimus calcium, a next generation DHODH inhibitor for the Treatment of relapsing-remitting multiple sclerosis", Multiple Sclerosis and Related Disorders, 2020, 43, 102129, published online May 5, 2020. DOI: 10.1016/j.msard.2020.102129.
Hahn F et al, "IMU-838, a Developmental DHODH Inhibitor in Phase II for Autoimmune Disease, Shows Anti-SARS-CoV-2 and Broad-Spectrum Antiviral Efficacy In Vitro", Viruses, 2020, 12, 1394, published online Dec. 5, 2020. DOI: 10.3390/v12121394.
Kim Y et al, "Novel Dihydroorotate Dehydrogenase Inhibitors with Potent Interferon-Independent Antiviral Activity against Mamarenaviruses In Vitro", Viruses, 2020, 12, 821, published online Jul. 29, 2020. DOI: 10.3390/v12080821.
Muehler A et al, "Safety, Tolerability and Pharmacokinetics of Vidofludimus calcium (IMU-838) After Single and Multiple Ascending Oral Doses in Healthy Male Subjects", European Journal of Drug Metabolism and Pharmacokinetics, 2020, 45(5), 557-573, published online May 2, 2020. DOI: 10.1007/s13318-020-00623-7.
Fox R et al, "Design, Rationale and Baseline Characteristics of the Randomized Double-blind Phase II Clinical Trial of Vidofludimus calcium (IMU-838) in Relapsing-Remitting Multiple Sclerosis (4558)", Neurology, 2020, 94 (15 Supplement), 4558, published online Apr. 14, 2020.
Muehler A et al, "The Selective Oral Immunomodulator Vidofludimus in Patients with Active Rheumatoid Arthritis: Safety Results from the Component Study", Drugs in R&D, 2019, 19(4), 351-366, published online Oct. 16, 2019. DOI: 10.1007/s40268-019-00286-z.
Marschall et al, "Assessment of drug candidates for broad-spectrum antiviral therapy targeting cellular pyrimidine biosynthesis", Antiviral Research, 2013, 100, 640-648, published online Oct. 20, 2013. DOI: 10.1016/j.antiviral.2013.10.003.
Fox et al, "Efficacy and safety of the selective oral DHODH modulator vidofludimus calcium (IMU-838) in relapsing-remitting multiple sclerosis: a randomized, placebo-controlled Phase 2 trial (EMPhASIS)", poster presentation at the 2021 Virtual AAN Annual Meeting, Apr. 17-22, 2021.
Kohlhof H et al, "Preclinical Investigations of IMU-838, an Orally Available Small Molecule Inhibitor of Dihydroorotate Dehydrogenase for the Treatment of Inflammatory Bowel Disease" poster presentation at United European Gastroenterology Week (UEGW), Barcelona, Spain, Oct. 22, 2019.
Immunic Announces FDA Clearance to Begin IMU-838 Phase 3 Ensure Studies in Relapsing-Remitting Multiple Sclerosis and Phase 2 Calliper Study in Progressive Multiple Sclerosis; press release, Immunic Inc, Jul. 1, 2021.
Immunic, Inc. Announces EMPhASIS Interim Analysis of 10 mg Cohort Confirms IMU-838's Dose Response in Relapsing-Remitting Multiple Sclerosis and Supports Phase 3 Dose Selection; press release, Immunic Inc, Apr. 15, 2021.
"Efficacy and Safety of the Selective Oral DHODH Modulator Vidofludimus Calcium (IMU-838)in Relapsing-Remitting Multiple Sclerosis:A Randomized, Placebo-Controlled Phase 2 Trial (EMPhASIS)" presentation at 2021 Virtual AAN Annual Meeting, Apr. 17-22, 2021.
"Immunic Inc RRMS-PMS Conference Call" held at Jul. 1, 2021.

* cited by examiner

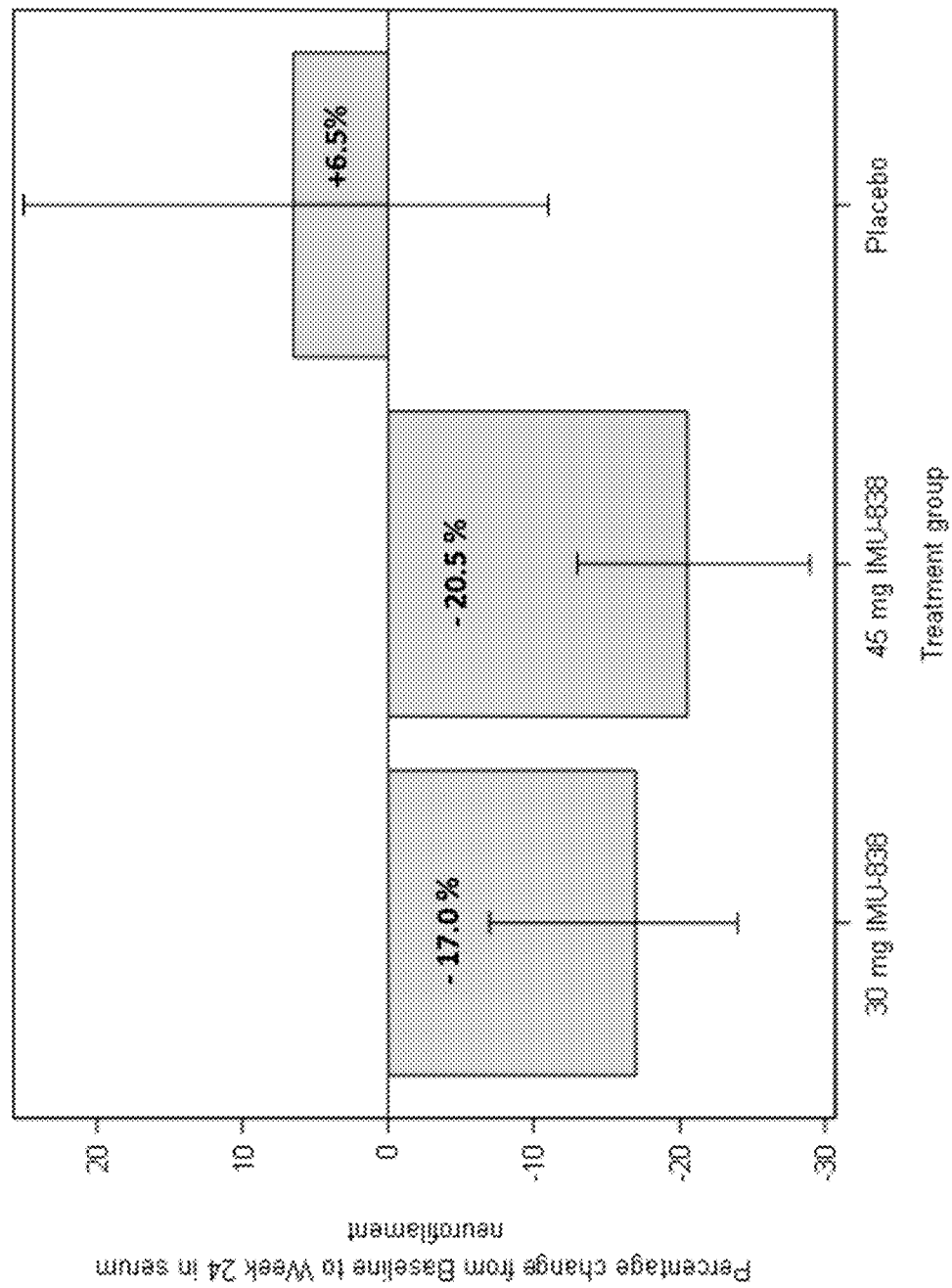

TREATMENT OF MULTIPLE SCLEROSIS COMPRISING DHODH INHIBITORS

SUMMARY OF THE INVENTION

The present invention relates to methods of treating or ameliorating multiple sclerosis by the dihydroorotate dehydrogenase (DHODH) inhibitor vidofludimus and/or a pharmaceutically acceptable salt and/or a solvate, in particular a hydrate, thereof and/or a solvate, in particular a hydrate, of a pharmaceutically acceptable salt thereof, comprising administering to a human patient a therapeutically effective amount of the DHODH inhibitor.

BACKGROUND, INTRODUCTION AND PRIOR ART

The immunopathogenesis of multiple sclerosis (MS) is characterized by pathogenic T- and B-cells that infiltrate the central nervous system and cause multifocal inflammation, demyelination, and neurodegeneration.

Current medications for MS which are disease modifying treatments, i.e. modifying the course of MS, modulate or suppress the immune system. There have been several FDA approved immunomodulating agents for relapsing-remitting MS (rrMS) in the past, including the following: three beta interferons (Betaseron®, Berlex; Avonex®, Biogen; Rebif®, Serono) and Glatiramer Acetate (Copaxone®, Teva). There is also one FDA approved immunosuppressing drug for worsening MS, Mitoxantrone (Novantrone®, Amgen). Several other immunosuppressive agents are used, although not FDA approved. However, meanwhile the arsenal of the so-called Disease Modifying Drugs (DMDs) or Disease Modifying Therapeutics/Therapies (DMTs) comprises the following:

Interferon beta-1a, Beta interferon-1a (e.g. Avonex®, Rebif®); Interferon beta-1 b, Beta interferon-1b (e.g. Betaferon®, Extavia®); Peginterferon beta 1a (e.g. Plegridy®); Alemtuzumab (e.g.) Lemtrada®; Daclizumab (e.g. Zinbryta®); Dimethyl fumarate (e.g. Tecfidera®); Diroximel fumarate (Vumerity®); Monomethyl fumarate (Bafiertam®); Fingolimod (e.g. Gilenya®); Glatiramer acetate (e.g. Copaxone®); Natalizumab (e.g. Tysabri®); Ocrelizumab (e.g. Ocrevus®); Ofatumumab (e.g. Kesimpta®); Cladribine (e.g. Mavenclad®); Siponimod (e.g. Mayzent); Ozanimod (e.g. Zeposia®); Ponesimod (e.g. Ponvory®) and Teriflunomide (e.g. Aubagio®).

Active and rapidly dividing lymphocytes meet their pyrimidine needs by highly expressing DHODH, a mitochondrial enzyme involved in the rate-limiting step of de novo pyrimidine synthesis, whereas resting lymphocytes are able to meet their pyrimidine needs through an DHODH-independent salvage pathway. Hence, DHODH blockage is of significant clinical interest in pathologies mediated by activated pathogenic lymphocyte populations. The role of DHODH in the pathogenesis of MS was demonstrated in the TEMSO and TOWER trials of teriflunomide, the only approved DHODH inhibitor in Europe and the US for relapsing forms of MS. Use of teriflunomide can be limited by its side effect profile: diarrhoea, alopecia, neutropenia, and elevated liver enzymes.

Vidofludimus calcium is a novel, orally available, highly selective inhibitor of DHODH in development for immune-mediated inflammatory diseases including relapsing MS, ulcerative colitis (NCT03341962), primary sclerosing cholangitis (NCT03722576) and coronavirus disease 2019 (NCT04379271; Viruses 2020; 12:1394.). Vidofludimus calcium has a half-life of approximately 30 h that allows for once-daily oral dosing and rapid wash-out at treatment discontinuation (Eur. J. Drug Metab. Pharmacokinet. 2020; 45:557), exhibited submicromolar potency against human DHODH and inhibited T-lymphocyte proliferation and secretion of interleukin (IL)-17 and IFNγ in vitro (Mult. Scler. Relat. Disord. 2020; 43:102129). Vidofludimus calcium demonstrated dose-dependent activity in experimental autoimmune encephalomyelitis in rodents. More than 800 healthy volunteers or patients with immune-related conditions have been exposed to vidofludimus in completed or ongoing trials. In the COMPONENT trial, patients with active rheumatoid arthritis treated with 35 mg vidofludimus free acid once-daily for 13 weeks had an overall similar safety profile as compared to placebo (Drugs R D 2019; 19:351). This included no notable increases in diarrhoea, alopecia, neutropenia or liver enzyme elevations.

Vidofludimus (Formula I) (2-((3-fluoro-3'-methoxy-[1,1'-biphenyl]-4-yl)carbamoyl)cyclopent-1-enecarboxylic acid) is an orally available DHODH inhibitors with no structural similarity to other known drugs, including leflunomide and teriflunomide. As described above, vidofludimus, in both its free acid form and its calcium salt formulation (vidofludimus calcium), has undergone clinical trials for a variety of immune-related indications. Both formulations depend on the same active substance (vidofludimus) in vivo, and thus the two formulations share the same mechanism of action, pharmacology and toxicology.

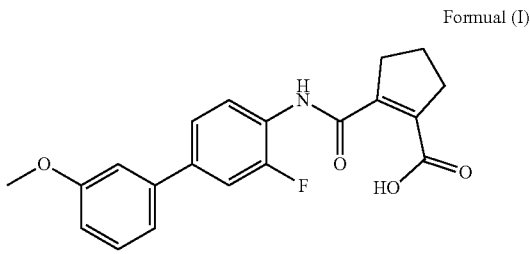 [SMILES: COc1cccc(-c2ccc(NC(=O)C3=C(C(=O)O)CCC3)c(F)c2)c1]

Formual (I)

WO 2003/006424 and WO 2003/006425 describe certain specific compounds, which are reported to be useful for treatment and prevention of diseases where there is an advantage in inhibiting DHODH. WO 2010/128050 and WO 2015/154820 describes the use of these compounds as broad antiviral agents. WO 2012/001148 describes calcium salts of the compound of Formula (I) which inhibit DHODH and the preparation thereof (example 4). WO 2012/001151 describes other salts of the compound according to Formula (I). WO 2019/175396 describes a new white crystalline calcium salt of vidofludimus and their solvates and hydrates (designated as "Polymorph A"), a process for its preparation, a composition comprising it and its use for the treatment of chronic inflammatory and/or autoimmune diseases.

To minimize the risk of changes to uric acid during the first days of dosing with vidofludimus or a pharmaceutically acceptable salt and/or solvate thereof, a dosing regimen has been described, which use only half of the maintenance dose (WO 2019/101888).

Based on new and surprisingly advantageous clinical results discussed herein in detail, without wishing to be bound by theory, it is believed that specific oral dosings, specific oral dosage forms and/or specific oral dose regimens described herein comprising the active ingredient vidofludimus and/or a pharmaceutically acceptable salt and/or a solvate, in particular a hydrate, thereof and/or a solvate, in particular a hydrate, of a pharmaceutically acceptable salt thereof, are effective in the treatment of MS, and especially effective for the treatment of rrMS and/or progressive MS (pMS), both with vidofludimus or a pharmaceutically acceptable salt or a solvate, in particular a hydrate, thereof or a solvate, in particular a hydrate, of a pharmaceutically acceptable salt thereof as a single agent and in combination with other DMDs.

In light of these findings, vidofludimus or a pharmaceutically acceptable salt or a solvate, in particular a hydrate, thereof or a solvate, in particular a hydrate, of a pharmaceutically acceptable salt thereof have the potential to be effective in treating relapsing multiple sclerosis with a potentially strong safety and tolerability profile. The results of a phase 2, multi-centre, double-blind, randomized controlled trial (NCT03846219; EudraCT 2018-001896-19) that investigated the safety and efficacy of vidofludimus calcium as compared to placebo in patients with rrMS is reported which allow the determination of the therapeutically effective daily dose of about 10 mg to 45 mg.

BRIEF SUMMARY OF THE INVENTION

The present invention is directed towards a method of treating a human patient afflicted with multiple sclerosis or presenting a clinically isolated syndrome, the method comprising orally administering to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg to 45 mg vidofludimus or a pharmaceutical acceptable salt thereof or solvate, in particular a hydrate, thereof or a solvate, in particular a hydrate, of a pharmaceutically acceptable salt thereof so as to thereby treat the human patient.

Especially, the efficacy of vidofludimus calcium dihydrate in the treatment of multiple sclerosis, in particular relapsing-remitting multiple sclerosis, can preferably be shown by significant improvements with regard to the cumulative number of combined unique active lesions up to 24 weeks when compared to placebo using an once-daily oral dose of vidofludimus calcium dihydrate of 30 mg or 45 mg. Additionally, vidofludimus calcium dihydrate demonstrated a favorable safety and tolerability profile with this two doses.

DETAILED DESCRIPTION OF THE INVENTION

Various (enumerated) embodiments of the present invention are described herein. It will be recognized that features specified in each embodiment may be combined with other specified features to provide further embodiments of the present disclosure.

Embodiments (a)

1a. The subject invention provides a method of treating a human patient afflicted with multiple sclerosis or presenting a clinically isolated syndrome, the method comprising orally administering to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg to 45 mg vidofludimus or a pharmaceutical acceptable salt thereof or solvate, in particular a hydrate, thereof or a solvate, in particular a hydrate, of a pharmaceutically acceptable salt thereof so as to thereby treat the human patient.

2a. The method comprising orally administering to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus so as to thereby treat the human patient.

3a. The method comprising orally administering to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

4a. The method comprising orally administering to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

5a. The administration of vidofludimus and/or a pharmaceutically acceptable salt thereof and/or a solvate, in particular a hydrate, thereof and/or a solvate, in particular a hydrate, of a pharmaceutically acceptable salt thereof is effective to alleviate a symptom of or a condition associated with multiple sclerosis.

6a. The administration of vidofludimus and/or a pharmaceutically acceptable salt thereof and/or a solvate, in particular a hydrate, thereof and/or a solvate, in particular a hydrate, of a pharmaceutically acceptable salt thereof is effective to increase the time to confirmed disease progression, increase the time to confirmed relapse, decrease the hazard ratio for time to confirmed relapse, reduce brain atrophy, reduce relapse rate, reduce rate of confirmed relapses requiring hospitalization, reduce or inhibit progression of the level of fatigue, improve or inhibit deterioration of the functional status, improve or inhibit deterioration of the general health, reduce MRI-monitored disease activity or reduce cognitive impairment in the human patient.

7a. The administration of vidofludimus and/or a pharmaceutically acceptable salt thereof and/or a solvate, in particular a hydrate, thereof and/or a solvate, in particular a hydrate, of a pharmaceutically acceptable salt thereof is effective to increase the time to confirmed disease progression in the human patient.

8a. Confirmed disease progression is measured by Kurtzke Expanded Disability Status Scale (EDSS) score.

9a. Confirmed disease progression is at least a 1 point increase of the EDSS score. In one embodiment, the patient had confirmed disease progression of at least a 0.5 point increase of the EDSS score.

10a. The hazard ratio for no confirmed disability worsening is decreased by 20-60%.

11a. The hazard ratio for no confirmed disability worsening is decreased by 30-50%.

12a. The hazard ratio for no confirmed disability worsening is decreased by at least 30%.

13a. The hazard ratio for no confirmed disability worsening is decreased by at least 40%.

14a. The hazard ratio for no confirmed disability worsening is decreased by at least 50%.

Embodiments (b)

1b. The administration of vidofludimus and/or a pharmaceutically acceptable salt thereof and/or a solvate, in particular a hydrate, thereof and/or a solvate, in particular a hydrate, of a pharmaceutically acceptable salt thereof effective to increase time to confirmed relapse in the human patient.

2b. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

3b. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or solvate, in particular a hydrate, thereof or a solvate, in particular a hydrate, of a pharmaceutically acceptable salt thereof so as to thereby treat the human patient.

4b. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or solvate, in particular a hydrate, thereof or a solvate, in particular a hydrate, of a pharmaceutically acceptable salt thereof so as to thereby treat the human patient.

5b. The administration of vidofludimus and/or a pharmaceutically acceptable salt thereof and/or a solvate, in particular a hydrate, thereof and/or a solvate, in particular a hydrate, of a pharmaceutically acceptable salt thereof effective to decrease the hazard ratio for relapse-free survival by at least 20%.

6b. The administration of vidofludimus and/or a pharmaceutically acceptable salt thereof and/or a solvate, in particular a hydrate, thereof and/or a solvate, in particular a hydrate, of a pharmaceutically acceptable salt thereof effective to decrease the hazard ratio for relapse-free survival by at least 30%.

7b. The administration of vidofludimus and/or a pharmaceutically acceptable salt thereof and/or a solvate, in particular a hydrate, thereof and/or a solvate, in particular a hydrate, of a pharmaceutically acceptable salt thereof effective to decrease the hazard ratio for relapse-free survival by at least 40%.

8b. The administration of vidofludimus and/or a pharmaceutically acceptable salt thereof and/or a solvate, in particular a hydrate, thereof and/or a solvate, in particular a hydrate, of a pharmaceutically acceptable salt thereof effective to decrease the hazard ratio for relapse-free survival by at least 50%.

9b. The administration of vidofludimus and/or a pharmaceutically acceptable salt thereof and/or a solvate, in particular a hydrate, thereof and/or a solvate, in particular a hydrate, of a pharmaceutically acceptable salt thereof effective to decrease the hazard ratio for time to confirmed relapse in the human patient.

10b. The administration of vidofludimus and/or a pharmaceutically acceptable salt thereof and/or a solvate, in particular a hydrate, thereof and/or a solvate, in particular a hydrate, of a pharmaceutically acceptable salt thereof effective to decrease the hazard ratio for time to confirmed relapse in the human patient by at least 25%.

11b. The administration of vidofludimus and/or a pharmaceutically acceptable salt thereof and/or a solvate, in particular a hydrate, thereof and/or a solvate, in particular a hydrate, of a pharmaceutically acceptable salt thereof effective to decrease the hazard ratio for time to confirmed relapse in the human patient by at least 30%.

12b. The administration of vidofludimus and/or a pharmaceutically acceptable salt thereof and/or a solvate, in particular a hydrate, thereof and/or a solvate, in particular a hydrate, of a pharmaceutically acceptable salt thereof effective to decrease the hazard ratio for time to confirmed relapse in the human patient by at least 40%.

Embodiments (c)

1c. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce brain atrophy in the human patient.

2c. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce brain atrophy by 15-40%.

3c. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce brain atrophy by at least 25%.

4c. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce brain atrophy by at least 30%.

5c. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce brain atrophy by at least 35%.

6c. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

7c. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

8c. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

Embodiments (d)

1d. The administration of vidofludimus and/or a pharmaceutically acceptable salt thereof and/or a solvate, in particular a hydrate, thereof and/or a solvate, in particular a hydrate, of a pharmaceutically acceptable salt thereof is effective to reduce the annualized relapse rate in the human patient.

2d. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce the annualized relapse rate in the human patient by at least 25%.

3d. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce the annualized relapse rate in the human patient by at least 30%.

4d. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce the annualized relapse rate in the human patient by at least 40%.

5d. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce the annualized relapse rate in the human patient by at least 50%.

6d. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce the annualized relapse rate in the human patient by at least 60%.

7d. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce the annualized relapse rate in the human patient by at least 70%.

8d. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

9d. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

10d. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

Embodiments (e)

1e. The administration of vidofludimus and/or a pharmaceutically acceptable salt thereof and/or a solvate, in particular a hydrate, thereof and/or a solvate, in particular a hydrate, of a pharmaceutically acceptable salt thereof to reduce patient's risk for a confirmed disease progression by at least 30% compared to a patient not receiving vidofludimus or a pharmaceutically acceptable salt thereof or a solvate, in particular a hydrate, thereof or a solvate, in particular a hydrate, of a pharmaceutically acceptable salt thereof treatment.

2e. The administration of vidofludimus and/or a pharmaceutically acceptable salt thereof and/or a solvate, in particular a hydrate, thereof and/or a solvate, in particular a hydrate, of a pharmaceutically acceptable salt thereof to reduce patient's risk for a confirmed disease progression by at least 35% compared to a patient not receiving vidofludimus or a pharmaceutically acceptable salt thereof or a solvate, in particular a hydrate, thereof or a solvate, in particular a hydrate, of a pharmaceutically acceptable salt thereof treatment.

3e. The administration of vidofludimus and/or a pharmaceutically acceptable salt thereof and/or a solvate, in particular a hydrate, thereof and/or a solvate, in particular a hydrate, of a pharmaceutically acceptable salt thereof to reduce patient's risk for a confirmed disease progression by at least 40% compared to a patient not receiving vidofludimus or a pharmaceutically acceptable salt thereof or a solvate, in particular a hydrate, thereof or a solvate, in particular a hydrate, of a pharmaceutically acceptable salt thereof treatment.

4e. The administration of vidofludimus and/or a pharmaceutically acceptable salt thereof and/or a solvate, in particular a hydrate, thereof and/or a solvate, in particular a hydrate, of a pharmaceutically acceptable salt thereof to reduce patient's risk for a confirmed disease progression within 3 months of administration.

5e. The administration of vidofludimus and/or a pharmaceutically acceptable salt thereof and/or a solvate, in particular a hydrate, thereof and/or a solvate, in particular a hydrate, of a pharmaceutically acceptable salt thereof to reduce patient's risk for a confirmed disease progression within 6 months of administration.

6e. The administration of vidofludimus and/or a pharmaceutically acceptable salt thereof and/or a solvate, in particular a hydrate, thereof and/or a solvate, in particular a hydrate, of a pharmaceutically acceptable salt thereof to reduce patient's risk for a confirmed disease progression within 12 months of administration.

7e. The administration of vidofludimus and/or a pharmaceutically acceptable salt thereof and/or a solvate, in particular a hydrate, thereof and/or a solvate, in particular a hydrate, of a pharmaceutically acceptable salt thereof to reduce patient's risk for a confirmed disease progression within 18 months of administration.

8e. The administration of vidofludimus and/or a pharmaceutically acceptable salt thereof and/or a solvate, in particular a hydrate, thereof and/or a solvate, in particular a hydrate, of a pharmaceutically acceptable salt thereof to reduce patient's risk for a confirmed disease progression within 24 months of administration.

9e. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

10e. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

11e. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

Embodiments (f)

1f. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce or inhibit progression of the level of fatigue in the human patient.

2f. The administration of vidofludimus and/or a pharmaceutically acceptable salt thereof and/or a solvate, in particular a hydrate, thereof and/or a solvate, in particular a hydrate, of a pharmaceutically acceptable salt thereof effective to improve or inhibit deterioration of the general health in the human patient.

3f. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce MRI-monitored disease activity in the human patient.

4f. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce MRI-monitored disease activity in the human patient as assessed by the number of T1 gadolinium-enhanced lesions, the number of new T2 lesions, the number of new T1 hypointense lesions (black holes), change in T2 lesions volume, change in gadolinium-enhanced lesions T1 volume or change in T1 hypointense lesions volume (black holes).

5f. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce MRI-monitored disease activity in the human patient as assessed by the cumulative number of enhancing lesions on T1-weighted images, the cumulative number of new hypointense lesions on T1-scans, and the cumulative number of new T2 lesions.

6f. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce MRI-monitored disease activity in the human patient as assessed by the mean cumulative number of gadolinium-enhanced lesions, gadolinium-enhanced lesions counts, change in T2 visible lesion or change in brain volume.

7f. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

8f. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

9f. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

Embodiments (g)

1g. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce cognitive impairment in the human patient.

2g. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

3g. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

4g. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

Embodiments (h)

1h. The administration of vidofludimus and/or a pharmaceutically acceptable salt thereof and/or a solvate, in particular a hydrate, thereof and/or a solvate, in particular a hydrate, of a pharmaceutically acceptable salt thereof as monotherapy for multiple sclerosis.

2h. The administration of vidofludimus and/or a pharmaceutically acceptable salt thereof and/or a solvate, in particular a hydrate, thereof and/or a solvate, in particular a hydrate, of a pharmaceutically acceptable salt thereof as adjunct therapy with another multiple sclerosis treatment.

3h. The administration of vidofludimus and/or a pharmaceutically acceptable salt thereof and/or a solvate, in particular a hydrate, thereof and/or a solvate, in particular a hydrate, of a pharmaceutically acceptable salt thereof as adjunct therapy with another multiple sclerosis treatment wherein the other relapsing-remitting multiple sclerosis treatment is administration of interferon beta 1-a, interferon beta 1-b, glatiramer acetate, mitoxantrone, ocrelizumab, natalizumab, alemtuzumab, dialkyl fumarate, laquinimod, siponimod or fingolimod.

4h. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

5h. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

6h. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

Embodiments (i)

1i. The administration of vidofludimus and/or a pharmaceutically acceptable salt thereof and/or a solvate, in particular a hydrate, thereof and/or a solvate, in particular a hydrate, of a pharmaceutically acceptable salt thereof effective to reduce cognitive impairment in the human patient.

2i. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

3i. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

4i. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or a solvate, in particular a hydrate, thereof or a solvate, in particular a hydrate, of a pharmaceutically acceptable salt thereof so as to thereby treat the human patient.

Embodiments (j)

1j. The administration of vidofludimus and/or a pharmaceutically acceptable salt thereof and/or a solvate, in particular a hydrate, thereof and/or a solvate, in particular a hydrate, of a pharmaceutically acceptable salt thereof for the treatment of relapsing-remitting multiple sclerosis.

2j. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutical acceptable salt thereof or a solvate, in particular a hydrate, thereof or a solvate, in particular a hydrate, of a pharmaceutically acceptable salt thereof for the treatment of relapsing-remitting multiple sclerosis.

3j. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or a solvate, in particular a hydrate, thereof or a solvate, in particular a hydrate, of a pharmaceutically acceptable salt thereof for the treatment of relapsing-remitting multiple sclerosis.

4j. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or a solvate, in particular a hydrate, thereof or a solvate, in particular a hydrate, of a pharmaceutically acceptable salt thereof for the treatment of relapsing-remitting multiple sclerosis.

Embodiments (k)

1k. The administration of vidofludimus and/or a pharmaceutically acceptable salt thereof and/or a solvate, in particular a hydrate, thereof and/or a solvate, in particular a hydrate, of a pharmaceutically acceptable salt thereof for providing neuroprotection to a human subject.

2k. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutical acceptable salt thereof or a solvate, in particular a hydrate, thereof or a solvate, in particular a hydrate, of a pharmaceutically acceptable salt thereof for providing neuroprotection to a human subject.

3k. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutical acceptable salt thereof or a solvate, in particular a hydrate, thereof or a solvate, in particular a hydrate, of a pharmaceutically acceptable salt thereof for providing neuroprotection to a human subject.

4k. The administration to the human patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutical acceptable salt thereof or a solvate, in particular a hydrate, thereof or a solvate, in particular a hydrate, of a pharmaceutically acceptable salt thereof for providing neuroprotection to a human subject.

Embodiments (l)

1l. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of substantially 10 mg to 45 mg vidofludimus or a pharmaceutically acceptable salt thereof/or a solvate, in particular a hydrate, thereof or a solvate, in particular a hydrate, of a pharmaceutically acceptable salt thereof.

2l. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of substantially 10 mg vidofludimus or a pharmaceutically acceptable salt thereof or a solvate, in particular a hydrate, thereof or a solvate, in particular a hydrate, of a pharmaceutically acceptable salt thereof.

3l. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of substantially 30 mg vidofludimus or a pharmaceutically acceptable salt thereof or a solvate, in particular a hydrate, thereof or a solvate, in particular a hydrate, of a pharmaceutically acceptable salt thereof.

4l. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of substantially 45 mg vidofludimus or a pharmaceutically acceptable salt thereof or a solvate, in particular a hydrate, thereof or a solvate, in particular a hydrate, of a pharmaceutically acceptable salt thereof.

5l. The method of any of the above embodiments comprising orally administering to the patient vidofludimus or a pharmaceutically acceptable salt thereof and/or a solvate, in particular a hydrate, thereof and/or a solvate, in particular a hydrate, of a pharmaceutically acceptable salt thereof in the form of vidofludimus calcium.

Embodiments (m)

1m. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of substantially 10 mg to 45 mg vidofludimus or a pharmaceutically acceptable salt thereof or a solvate, in particular a hydrate, thereof or a solvate, in particular a hydrate, of a pharmaceutically acceptable salt thereof for a period of equal or greater than 24 weeks.

2m. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of substantially 10 mg to 45 mg vidofludimus or a pharmaceutically acceptable salt thereof or a solvate, in particular a hydrate, thereof or a solvate, in particular a hydrate, of a pharmaceutically acceptable salt thereof for a period of equal or greater than 72 weeks.

3m. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of substantially 10 mg to 45 mg vidofludimus or a pharmaceutically acceptable salt thereof or a solvate, in particular a hydrate, thereof or a solvate, in particular a hydrate, of a pharmaceutically acceptable salt thereof for a period of equal or greater than 2 years.

4m. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of substantially 10 mg vidofludimus or a pharmaceutically acceptable salt thereof or a solvate, in particular a hydrate, thereof or a solvate, in particular a hydrate, of a pharmaceutically acceptable salt thereof.

5m. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of substantially 30 mg vidofludimus or a pharmaceutically acceptable salt thereof or a solvate, in particular a hydrate, thereof or a solvate, in particular a hydrate, of a pharmaceutically acceptable salt thereof.

6m. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of substantially 45 mg vidofludimus or a pharmaceutically acceptable salt thereof or a solvate, in particular a hydrate, thereof or a solvate, in particular a hydrate, of a pharmaceutically acceptable salt thereof.

Embodiments (n)

1n. A method of treating a human patient afflicted with multiple sclerosis or presenting a clinically isolated syndrome by increasing the time to confirmed disease progression, increasing the time to confirmed relapse or reducing brain atrophy in the human patient, the method comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg to 45 mg vidofludimus or a pharmaceutically acceptable salt thereof or a solvate, in particular a hydrate, thereof or a solvate, in particular a hydrate, of a pharmaceutically acceptable salt thereof so as to thereby treat the human patient by increasing the time to confirmed disease progression, increasing the time to confirmed relapse or reducing brain atrophy in the human patient.

2n. A method of treating a human patient afflicted with multiple sclerosis or presenting a clinically isolated syndrome by increasing the time to confirmed disease progression, increasing the time to confirmed relapse or reducing brain atrophy in the human patient, the method comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 10 mg vidofludimus or a pharmaceutically acceptable salt thereof or a solvate, in particular a hydrate, thereof or a solvate, in particular a hydrate, of a pharmaceutically acceptable salt thereof so as to thereby treat the human patient by increasing the time to confirmed disease progression, increasing the time to confirmed relapse or reducing brain atrophy in the human patient.

3n. A method of treating a human patient afflicted with multiple sclerosis or presenting a clinically isolated syndrome by increasing the time to confirmed disease progression, increasing the time to confirmed relapse or reducing brain atrophy in the human patient, the method comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg vidofludimus or a pharmaceutically acceptable salt thereof or a solvate, in particular a hydrate, thereof or a solvate, in particular a hydrate, of a pharmaceutically acceptable salt thereof so as to thereby treat the human patient by increasing the time to confirmed disease progression, increasing the time to confirmed relapse or reducing brain atrophy in the human patient.

4n. A method of treating a human patient afflicted with multiple sclerosis or presenting a clinically isolated syndrome by increasing the time to confirmed disease progression, increasing the time to confirmed relapse or reducing brain atrophy in the human patient, the method comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 45 mg vidofludimus or a pharmaceutically acceptable salt thereof or a solvate, in particular a hydrate, thereof or a solvate, in particular a hydrate, of a pharmaceutically acceptable salt thereof so as to thereby treat the human patient by increasing the time to confirmed disease progression, increasing the time to confirmed relapse or reducing brain atrophy in the human patient.

Embodiments (o)

1o. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof in the form of a tablet.

2o. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof in the form of a capsule.

3o. The method of any of the above embodiments comprising a pharmaceutical oral unit dosage form containing substantially 10 mg to 45 mg vidofludimus and/or a pharmaceutically acceptable salt thereof and/or a solvate, in particular a hydrate, thereof and/or a solvate, in particular a hydrate, of a pharmaceutically acceptable salt thereof.

4o. The method of any of the above embodiments comprising a pharmaceutical oral unit dosage form containing substantially 10 mg vidofludimus and/or a pharmaceutically acceptable salt thereof and/or a solvate, in particular a hydrate, thereof and/or a solvate, in particular a hydrate, of a pharmaceutically acceptable salt thereof.

5o. The method of any of the above embodiments comprising a pharmaceutical oral unit dosage form containing substantially 30 mg vidofludimus and/or a pharmaceutically acceptable salt thereof and/or a solvate, in particular a hydrate, thereof and/or a solvate, in particular a hydrate, of a pharmaceutically acceptable salt thereof.

6o. The method of any of the above embodiments comprising a pharmaceutical oral unit dosage form containing substantially 45 mg vidofludimus and/or a pharmaceutically acceptable salt thereof and/or a solvate, in particular a hydrate, thereof and/or a solvate, in particular a hydrate, of a pharmaceutically acceptable salt thereof.

Embodiments (p)

1p. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof.

2p. The method of any of the above embodiments comprising orally administering to the patient vidofludimus in the form of the vidofludimus calcium salt dihydrate with the following structure:

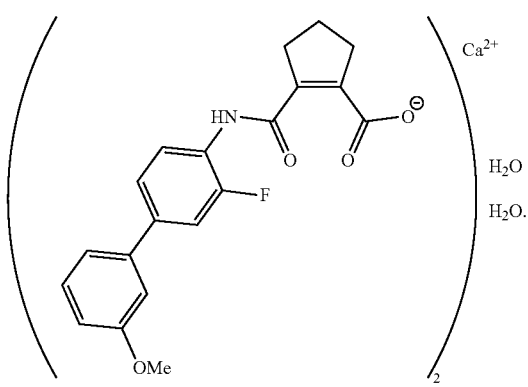

3p. The method of any of the above embodiments comprising orally administering to the patient vidofludimus in the form of "Polymorph A" of the vidofludimus calcium salt dihydrate characterized by an X-ray powder diffraction pattern having characteristic peaks at 2 theta (±0.2°) of 5.91°, 9.64°, 16.78°, 17.81°, 19.81° and 25.41°.

4p. The method of any of the above embodiments comprising orally administering to the patient vidofludimus in the form of "Polymorph A" of the vidofludimus calcium salt dihydrate characterized by an FT Raman absorption spectrum having the following characteristic peaks expressed in $cm^{-1}$ 1664, 1624, 1617, 1532, 1449 and 1338.

5p. The method of any of the above embodiments comprising orally administering to the patient vidofludimus in the form of "Polymorph A" of the vidofludimus calcium salt dihydrate characterized by an IR absorption spectrum having characteristic peaks expressed in $cm^{-1}$ 1980, 1659, 1584, 1335 and 1145.

6p. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 30 mg to about 45 mg vidofludimus or a pharmaceutically acceptable salt thereof or a solvate, in particular a hydrate, thereof or a solvate, in particular a hydrate, of a pharmaceutically acceptable salt thereof.

7p. The method of any of the above embodiments comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof at a daily dose of about 27 mg to about 45 mg vidofludimus or a pharmaceutically acceptable salt thereof or a solvate, in particular a hydrate, thereof or a solvate, in particular a hydrate, of a pharmaceutically acceptable salt thereof.

Embodiments (q)

1q. For the foregoing embodiments, each embodiment disclosed herein is contemplated as being applicable to each of the other disclosed embodiment.

2q. A pharmaceutically acceptable salt of vidofludimus as used in this application includes lithium, sodium, potassium, magnesium, calcium, manganese, copper, zinc, aluminium, iron, and ammonium derivatives. Salt formulations of vidofludimus and the process for preparing the same are described, e.g., in U.S. Patent Application Publication No. 2012/0035175, 2012/0029034 and 2021/0017125, and PCT International Application Publication No. WO 2012/001151, 2012/001148 and 2019/175396, which are hereby incorporated by reference into this application.

3q. A dosage unit may comprise a single compound or mixtures of compounds thereof. A dosage unit can be prepared for oral dosage forms, such as tablets, capsules, pills, powders, and granules.

4q. Vidofludimus and/or a pharmaceutically acceptable salt thereof and/or a solvate, in particular a hydrate, thereof and/or a solvate, in particular a hydrate, of a pharmaceutically acceptable salt thereof can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral administration. vidofludimus and/or a pharmaceutically acceptable salt thereof and/or a solvate, in particular a hydrate, thereof and/or a solvate, in particular a hydrate, of a pharmaceutically acceptable salt thereof can be administered alone but is generally mixed with a pharmaceutically acceptable carrier and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents flow-inducing agents, and melting agents.

Embodiments (r)

1r. Vidofludimus and/or a pharmaceutically acceptable salt and/or a solvate, in particular a hydrate, thereof and/or a solvate, in particular a hydrate, of a pharmaceutically acceptable salt thereof for use in a method of treating a human patient afflicted with multiple sclerosis the method comprising orally administering to the human patient vidofludimus and/or a pharmaceutically acceptable salt and/or a solvate, in particular a hydrate, thereof and/or a solvate, in particular a hydrate, of a pharmaceutically acceptable salt thereof at a daily dose of about 10 mg to 45 mg vidofludimus or a pharmaceutically acceptable salt or a solvate, in particular a hydrate, thereof or a solvate, in particular a hydrate, of a pharmaceutically acceptable salt thereof so as to thereby treat the human patient.

2r. Vidofludimus and/or a pharmaceutically acceptable salt and/or a solvate, in particular a hydrate, thereof and/or a solvate, in particular a hydrate, of a pharmaceutically acceptable salt thereof for use in the method of embodiment 1r, wherein the administration of vidofludimus and/or a pharmaceutically acceptable salt and/or a solvate, in particular a hydrate, thereof and/or a solvate, in particular a hydrate, of a pharmaceutically acceptable salt thereof is effective to alleviate a symptom of or a condition associated with multiple sclerosis.

3r. Vidofludimus and/or a pharmaceutically acceptable salt and/or a solvate, in particular a hydrate, thereof and/or a solvate, in particular a hydrate, of a pharmaceutically acceptable salt thereof for use in the method of embodiment 2r, wherein the administration of vidofludimus and/or a pharmaceutically acceptable salt and/or a solvate, in particular a hydrate, thereof and/or a solvate, in particular a hydrate, of a pharmaceutically acceptable salt thereof is effective to reduce relapse rate, reduce rate of confirmed relapses requiring hospitalization and/or IV steroids, reduce the accumulation of disability, reduce or inhibit progression of the level of fatigue, improve or inhibit deterioration of the functional status, improve or inhibit deterioration of the general health, reduce MRI-monitored disease activity or reduce cognitive impairment in the human patient.

4r. Vidofludimus and/or a pharmaceutically acceptable salt and/or a solvate, in particular a hydrate, thereof and/or a solvate, in particular a hydrate, of a pharmaceutically acceptable salt thereof for use in the method of embodiment 3r, wherein the administration of vidofludimus and/or a pharmaceutically acceptable salt and/or a solvate, in particular a hydrate, thereof and/or a solvate, in particular a hydrate, of a pharmaceutically acceptable salt thereof is effective to decrease the hazard ratio for time to confirmed relapse in the human patient.

5r. Vidofludimus and/or a pharmaceutically acceptable salt and/or a solvate, in particular a hydrate, thereof and/or a solvate, in particular a hydrate, of a pharmaceutically acceptable salt thereof for use in the method of embodiment 3r, wherein the administration of vidofludimus and/or a pharmaceutically acceptable salt and/or solvate, in particular hydrate, thereof and/or a solvate, in particular hydrate, of a pharmaceutically acceptable salt thereof is effective to reduce the annualized relapse rate in the human patient.

6r. Vidofludimus and/or a pharmaceutically acceptable salt and/or a solvate, in particular a hydrate, thereof and/or a solvate, in particular a hydrate, of a pharmaceutically acceptable salt thereof for use in the method embodiment 5r, wherein the relapse rate is reduced by at least 25%.

7r. Vidofludimus and/or a pharmaceutically acceptable salt and/or a solvate, in particular a hydrate, thereof and/or a solvate, in particular a hydrate, of a pharmaceutically acceptable salt thereof for use in the method of embodiment 3r, wherein the administration of vidofludimus and/or a pharmaceutically acceptable salt and/or a solvate, in particular a hydrate, thereof and/or a solvate, in particular a hydrate, of a pharmaceutically acceptable salt thereof is effective to improve or inhibit deterioration of the general health in the human patient.

8r. Vidofludimus and/or a pharmaceutically acceptable salt and/or a solvate, in particular a hydrate, thereof and/or a solvate, in particular a hydrate, of a pharmaceutically acceptable salt thereof for use in the method of any one of embodiments 1r-7r, wherein the vidofludimus and/or a pharmaceutically acceptable salt and/or a solvate, in particular a hydrate, thereof and/or a solvate, in particular a hydrate, of a pharmaceutically acceptable salt thereof is administered as monotherapy for multiple sclerosis.

9r. Vidofludimus and/or a pharmaceutically acceptable salt and/or a solvate, in particular a hydrate, thereof and/or a solvate, in particular a hydrate, of a pharmaceutically acceptable salt thereof for use in the method of any one of embodiments 1r-7r, wherein the vidofludimus and/or a pharmaceutically acceptable salt and/or a solvate, in particular a hydrate, thereof and/or a solvate, in particular a hydrate, of a pharmaceutically acceptable salt thereof is administered as adjunct therapy with another multiple sclerosis treatment.

10r. Vidofludimus and/or a pharmaceutically acceptable salt and/or a solvate, in particular a hydrate, thereof and/or a solvate, in particular a hydrate, of a pharmaceutically acceptable salt thereof for use in the method of embodiment 9r, wherein the other multiple sclerosis treatment is administration of interferon beta 1-a, interferon beta 1-b, glatiramer acetate, mitoxantrone, ocrelizumab, natalizumab, alemtuzumab, dialkyl fumarate, laquinimod, siponimod or fingolimod.

11r. Vidofludimus and/or a pharmaceutically acceptable salt and/or a solvate, in particular a hydrate, thereof and/or a solvate, in particular a hydrate, of a pharmaceutically acceptable salt thereof for use in the method of any one of embodiments 1r-10r, wherein the human patient is afflicted with relapsing-remitting multiple sclerosis.

12r. Vidofludimus and/or a pharmaceutically acceptable salt and/or a solvate, in particular a hydrate, thereof and/or a solvate, in particular a hydrate, of a pharmaceutically acceptable salt thereof for use in the method of any one of embodiments 1r-10r, wherein the human patient is afflicted with progressive multiple sclerosis.

13r. Vidofludimus and/or a pharmaceutically acceptable salt and/or a solvate, in particular a hydrate, thereof and/or a solvate, in particular a hydrate, of a pharmaceutically acceptable salt thereof for use in a method for treating a human subject by providing neuroprotection to the human subject comprising orally administering to the human subject a daily dose of about 10 mg to 45 mg vidofludimus or a pharmaceutically acceptable salt or a solvate, in particular a hydrate, thereof or a solvate, in particular a hydrate, of a pharmaceutically acceptable salt thereof so as to thereby treat the human subject by providing neuroprotection to the human subject.

14r. Vidofludimus and/or a pharmaceutically acceptable salt and/or a solvate, in particular a hydrate, thereof and/or a solvate, in particular a hydrate, of a pharmaceutically acceptable salt thereof for use in a method of embodiment 11, the method comprising orally administering to the patient vidofludimus and/or a pharmaceutically acceptable salt and/or a solvate, in particular a hydrate, thereof or a solvate, in particular a hydrate, of a pharmaceutically acceptable salt thereof at a daily dose of about 10 mg to 45 mg vidofludimus or a pharmaceutically acceptable salt or a solvate, in particular a hydrate, thereof or a solvate, in particular a hydrate, of a pharmaceutically acceptable salt thereof so as to thereby treat the human patient by increasing the time to confirmed disease progression, decreasing the hazard ratio for time to confirmed relapse, increasing the time to confirmed relapse or reducing brain atrophy in the human patient.

15r. Vidofludimus and/or a pharmaceutically acceptable salt and/or a solvate, in particular a hydrate, thereof and/or a solvate, in particular a hydrate, of a pharmaceutically acceptable salt thereof for use in the method of embodiment 14, wherein the administration of vidofludimus and/or a pharmaceutically acceptable salt and/or a solvate, in particular a hydrate, thereof and/or a solvate, in particular a hydrate, of a pharmaceutically acceptable salt thereof is effective to decrease the hazard ratio for time to confirmed relapse in the human patient.

16r. Vidofludimus and/or a pharmaceutically acceptable salt and/or a solvate, in particular a hydrate, thereof and/or a solvate, in particular a hydrate, of a pharmaceutically acceptable salt thereof for use in the method of any one of embodiments 14r-15r, wherein the vidofludimus and/or a pharmaceutically acceptable salt and/or a solvate, in particular a hydrate, thereof and/or a solvate, in particular a hydrate, of a pharmaceutically acceptable salt thereof is administered as monotherapy for relapsing-remitting multiple sclerosis.

17r. Vidofludimus and/or a pharmaceutically acceptable salt and/or a solvate, in particular a hydrate, thereof and/or a solvate, in particular a hydrate, of a pharmaceutically acceptable salt thereof for use in the method of any one of embodiments 14r-16r, wherein the human patient is afflicted with progressive multiple sclerosis.

18r. Vidofludimus and/or a pharmaceutically acceptable salt and/or a solvate, in particular a hydrate, thereof and/or a solvate, in particular a hydrate, of a pharmaceutically acceptable salt thereof for use in the method of embodiments 17r, comprising orally administering to the human patient or subject vidofludimus and/or a pharmaceutically acceptable salt and/or a solvate, in particular a hydrate, thereof and/or a solvate, in particular a hydrate, of a pharmaceutically acceptable salt thereof at a daily dose of about 10 mg to 45 mg vidofludimus or a pharmaceutically acceptable salt or a solvate, in particular a hydrate, thereof or a solvate, in particular a hydrate, of a pharmaceutically acceptable salt thereof.

19r. Vidofludimus for use in the method of any one of embodiments 1r-18r, wherein the vidofludimus is administered in the form of the vidofludimus calcium salt dihydrate with the following structure:

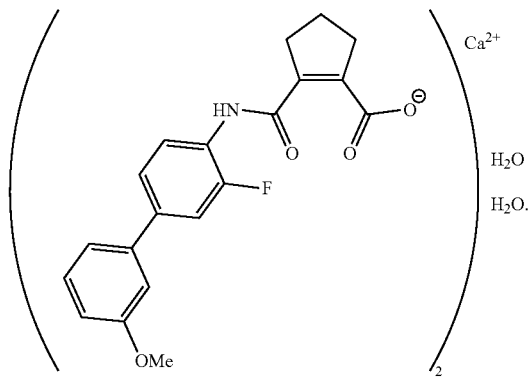

20r. Vidofludimus and/or a pharmaceutically acceptable salt and/or a solvate, in particular a hydrate, thereof and/or a solvate, in particular a hydrate, of a pharmaceutically acceptable salt thereof for use in the method of any of embodiments 1r-19r comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof in the form of a tablet or a capsule.

21r. Vidofludimus and/or a pharmaceutically acceptable salt and/or a solvate, in particular a hydrate, thereof or a solvate, in particular a hydrate, of a pharmaceutically acceptable salt thereof for use in a method of treating a human patient afflicted with multiple sclerosis of any of the above embodiments.

Embodiments (s)

1s. Use of vidofludimus and/or a pharmaceutically acceptable salt and/or a solvate, in particular a hydrate, thereof and/or a solvate, in particular a hydrate, of a pharmaceutically acceptable salt thereof for the manufacture of a medicament for the treatment a human patient afflicted with multiple sclerosis the method comprising orally administering to the human patient vidofludimus and/or a pharmaceutically acceptable salt and/or a solvate, in particular a hydrate, thereof and/or a solvate, in particular a hydrate, of a pharmaceutically acceptable salt thereof at a daily dose of about 10 mg to 45 mg vidofludimus or a pharmaceutically acceptable salt or a solvate, in particular a hydrate, thereof or a solvate, in particular a hydrate, of a pharmaceutically acceptable salt thereof so as to thereby treat the human patient.

2s. Use of vidofludimus and/or a pharmaceutically acceptable salt and/or a solvate, in particular a hydrate, thereof and/or a solvate, in particular a hydrate, of a pharmaceutically acceptable salt thereof of embodiment 1s, wherein the administration of vidofludimus and/or a pharmaceutically acceptable salt and/or a solvate, in particular a hydrate, thereof and/or a solvate, in particular a hydrate, of a pharmaceutically acceptable salt thereof is effective to alleviate a symptom of or a condition associated with multiple sclerosis.

3s. Use of vidofludimus and/or a pharmaceutically acceptable salt and/or a solvate, in particular a hydrate, thereof and/or a solvate, in particular a hydrate, of a pharmaceutically acceptable salt thereof of embodiment 2s, wherein the administration of vidofludimus and/or a pharmaceutically acceptable salt and/or a solvate, in particular a hydrate, thereof and/or a solvate, in particular a hydrate, of a pharmaceutically acceptable salt thereof is effective to reduce relapse rate, reduce rate of confirmed relapses requiring hospitalization and/or IV steroids, reduce the accumulation of disability, reduce or inhibit progression of the level of fatigue, improve or inhibit deterioration of the functional status, improve or inhibit deterioration of the general health, reduce MRI-monitored disease activity or reduce cognitive impairment in the human patient.

4s. Use of vidofludimus and/or a pharmaceutically acceptable salt and/or a solvate, in particular a hydrate, thereof and/or a solvate, in particular a hydrate, of a pharmaceutically acceptable salt thereof of embodiment 3s, wherein the administration of vidofludimus and/or a pharmaceutically acceptable salt and/or a solvate, in particular a hydrate, thereof and/or a solvate, in particular a hydrate, of a pharmaceutically acceptable salt thereof is effective to decrease the hazard ratio for time to confirmed relapse in the human patient.

5s. Use of vidofludimus and/or a pharmaceutically acceptable salt and/or a solvate, in particular a hydrate, thereof and/or a solvate, in particular a hydrate, of a pharmaceutically acceptable salt thereof of embodiment 3s, wherein the administration of vidofludimus and/or a pharmaceutically acceptable salt and/or solvate, in particular hydrate, thereof and/or a solvate, in particular hydrate, of a pharmaceutically acceptable salt thereof is effective to reduce the annualized relapse rate in the human patient.

6s. Use of vidofludimus and/or a pharmaceutically acceptable salt and/or a solvate, in particular a hydrate, thereof and/or a solvate, in particular a hydrate, of a pharmaceutically acceptable salt thereof of embodiment 5s, wherein the relapse rate is reduced by at least 25%.

7s. Use of vidofludimus and/or a pharmaceutically acceptable salt and/or a solvate, in particular a hydrate, thereof and/or a solvate, in particular a hydrate, of a pharmaceutically acceptable salt thereof of embodiment 3s, wherein the administration of vidofludimus and/or a pharmaceutically acceptable salt and/or a solvate, in particular a hydrate, thereof and/or a solvate, in particular a hydrate, of a pharmaceutically acceptable salt thereof is effective to improve or inhibit deterioration of the general health in the human patient.

8s. Use of vidofludimus and/or a pharmaceutically acceptable salt and/or a solvate, in particular a hydrate, thereof and/or a solvate, in particular a hydrate, of a pharmaceutically acceptable salt thereof of any one of embodiments 1s-7s, wherein the vidofludimus and/or a pharmaceutically acceptable salt and/or a solvate, in particular a hydrate, thereof and/or a solvate, in particular a hydrate, of a pharmaceutically acceptable salt thereof is administered as monotherapy for multiple sclerosis.

9s. Use of vidofludimus and/or a pharmaceutically acceptable salt and/or a solvate, in particular a hydrate, thereof and/or a solvate, in particular a hydrate, of a pharmaceutically acceptable salt thereof any one of embodiments 1s-7s, wherein the vidofludimus and/or a pharmaceutically acceptable salt and/or a solvate, in particular a hydrate, thereof and/or a solvate, in particular a hydrate, of a pharmaceutically acceptable salt thereof is administered as adjunct therapy with another multiple sclerosis treatment.

10s. Use of vidofludimus and/or a pharmaceutically acceptable salt and/or a solvate, in particular a hydrate, thereof and/or a solvate, in particular a hydrate, of a pharmaceutically acceptable salt thereof of embodiment 9s, wherein the other multiple sclerosis treatment is administration of interferon beta 1-a, interferon beta 1-b, glatiramer acetate, mitoxantrone, ocrelizumab, natalizumab, alemtuzumab, dialkyl fumarate, laquinimod, siponimod or fingolimod.

11s. Use of vidofludimus and/or a pharmaceutically acceptable salt and/or a solvate, in particular a hydrate, thereof and/or a solvate, in particular a hydrate, of a pharmaceutically acceptable salt thereof of any one of embodiments 1s-10s, wherein the human patient is afflicted with relapsing-remitting multiple sclerosis.

12s. Use of vidofludimus and/or a pharmaceutically acceptable salt and/or a solvate, in particular a hydrate, thereof and/or a solvate, in particular a hydrate, of a pharmaceutically acceptable salt thereof of any one of embodiments 1s-10s, wherein the human patient is afflicted with progressive multiple sclerosis.

13s. Use of vidofludimus and/or a pharmaceutically acceptable salt and/or a solvate, in particular a hydrate, thereof and/or a solvate, in particular a hydrate, of a pharmaceutically acceptable salt thereof for the manufacture of a medicament for the treatment a human subject by providing neuroprotection to the human subject comprising orally administering to the human subject a daily dose of about 10 mg to 45 mg vidofludimus or a pharmaceutically acceptable salt or a solvate, in particular a hydrate, thereof or a solvate, in particular a hydrate, of a pharmaceutically acceptable salt thereof so as to thereby treat the human subject by providing neuroprotection to the human subject.

14s. Use of vidofludimus and/or a pharmaceutically acceptable salt and/or a solvate, in particular a hydrate, thereof and/or a solvate, in particular a hydrate, of a pharmaceutically acceptable salt thereof of embodiment 11, the method comprising orally administering to the patient vidofludimus and/or a pharmaceutically acceptable salt and/or a solvate, in particular a hydrate, thereof or a solvate, in particular a hydrate, of a pharmaceutically acceptable salt thereof at a daily dose of about 10 mg to 45 mg vidofludimus or a pharmaceutically acceptable salt or a solvate, in particular a hydrate, thereof or a solvate, in particular a hydrate, of a pharmaceutically acceptable salt thereof so as to thereby treat the human patient by increasing the time to confirmed disease progression, decreasing the hazard ratio for time to confirmed relapse, increasing the time to confirmed relapse or reducing brain atrophy in the human patient.

15s. Use of vidofludimus and/or a pharmaceutically acceptable salt and/or a solvate, in particular a hydrate, thereof and/or a solvate, in particular a hydrate, of a pharmaceutically acceptable salt thereof of embodiment 14s, wherein the administration of vidofludimus and/or a pharmaceutically acceptable salt and/or a solvate, in particular a hydrate, thereof and/or a solvate, in particular a hydrate, of a pharmaceutically acceptable salt thereof is effective to decrease the hazard ratio for time to confirmed relapse in the human patient.

16s. Use of vidofludimus and/or a pharmaceutically acceptable salt and/or a solvate, in particular a hydrate, thereof and/or a solvate, in particular a hydrate, of a pharmaceutically acceptable salt thereof of any one of embodiments 14s-15s, wherein the vidofludimus and/or a pharmaceutically acceptable salt and/or a solvate, in particular a hydrate, thereof and/or a solvate, in particular a hydrate, of a pharmaceutically acceptable salt thereof is administered as monotherapy for relapsing-remitting multiple sclerosis.

17s. Use of vidofludimus and/or a pharmaceutically acceptable salt and/or a solvate, in particular a hydrate, thereof and/or a solvate, in particular a hydrate, of a pharmaceutically acceptable salt thereof of any one of embodiments 14s-16s, wherein the human patient is afflicted with progressive multiple sclerosis.

18s. Use of vidofludimus and/or a pharmaceutically acceptable salt and/or a solvate, in particular a hydrate, thereof and/or a solvate, in particular a hydrate, of a pharmaceutically acceptable salt thereof of embodiment 17s, comprising orally administering to the human patient or subject vidofludimus and/or a pharmaceutically acceptable salt and/or a solvate, in particular a hydrate, thereof and/or a solvate, in particular a hydrate, of a pharmaceutically acceptable salt thereof at a daily dose of about 10 mg to 45 mg vidofludimus or a pharmaceutically acceptable salt or a solvate, in particular a hydrate, thereof or a solvate, in particular a hydrate, of a pharmaceutically acceptable salt thereof.

19s. Use of Vidofludimus of any one of embodiments 1r-18r, wherein the vidofludimus is administered in the form of the vidofludimus calcium salt dihydrate with the following structure:

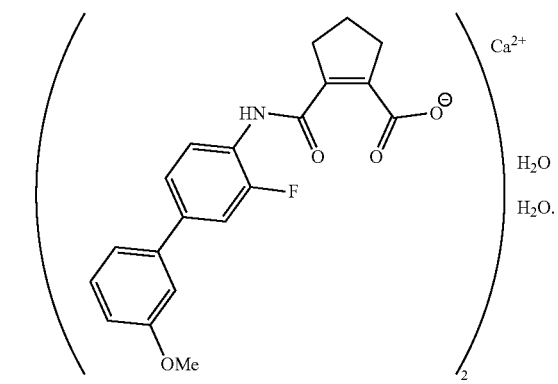

20s. Use of vidofludimus and/or a pharmaceutically acceptable salt and/or a solvate, in particular a hydrate, thereof and/or a solvate, in particular a hydrate, of a pharmaceutically acceptable salt thereof of any of embodiments 1s-19s comprising orally administering to the patient vidofludimus and/or a pharmaceutically acceptable salt thereof and/or a solvate, in particular a hydrate, thereof and/or a solvate, in particular a hydrate, of a pharmaceutically acceptable salt thereof in the form of a tablet or a capsule.

21s. Use of vidofludimus and/or a pharmaceutically acceptable salt and/or a solvate, in particular a hydrate, thereof or a solvate, in particular a hydrate, of a pharmaceutically acceptable salt thereof for the manufacture of a medicament for the treatment of a human patient afflicted with multiple sclerosis of any of the above embodiments.

Definitions

The term "vidofludimus" relates to the orally bioavailable DHODH inhibitor 2-((3-fluoro-3'-methoxy-[1,1'-biphenyl]-4-yl)carbamoyl)cyclopent-1-enecarboxylic acid) with chemical Formula (I):

Formula (I)

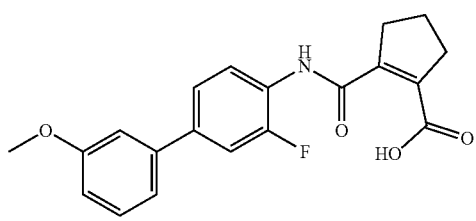

The preparation and characterization of pharmaceutically acceptable salts have been described in WO 2012/001151 (US 2012/0035175) and more specifically for calcium salts of vidofludimus in WO 2012/001148 (US 2012/0029034) and WO 2019/175396 (US 2021/0017125). The term "vidofludimus calcium" describes all polymorphs of the dihydrate of 1-cyclopentene-1-carboxylic acid, 2-(((3-fluoro-3'-methoxy(1,1'-biphenyl)-4-yl)amino)carbonyl)-, calcium salt (2:1) with the following chemical formula:

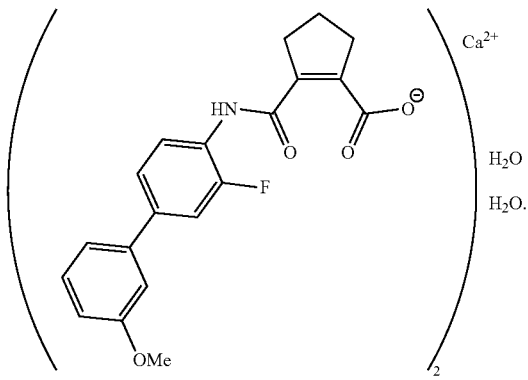

The term "IMU-838" describes one polymorph of "vidofludimus calcium" whose preparation and characterization is described in WO 2019/175396 (US 2021/0017125) as "Polymorph A". This "Polymorph A" is characterized by (a) an X-ray powder diffraction pattern having characteristic peaks at 2 theta (±0.2°) of 5.91°, 9.64°, 16.78°, 17.81°, 19.81° and 25.41°; and/or (b) an FT Raman absorption spectrum having the following characteristic peaks expressed in $cm^{-1}$ 1664, 1624, 1617, 1532, 1449 and 1338, and/or (c) an IR absorption spectrum having characteristic peaks expressed in $cm^{-1}$ 1980, 1659, 1584, 1335 and 1145.

The term "pharmaceutically acceptable salts" refers to salts prepared from pharmaceutically acceptable non-toxic bases, including inorganic bases and organic bases. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The respective salts can be obtained by customary methods which are known to the person skilled in the art like, for example, by contacting these with an organic or inorganic base in a solvent or dispersant, or by cation exchange with other salts. The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts.

The term "solvate" refers to a crystalline form of a molecule that further comprises molecules of a solvent or solvents incorporated into the crystalline lattice structure. Thus, the compounds of the present disclosure may be present in the form of solvates, such as those which include as solvate water, or pharmaceutically acceptable solvates, such as alcohols, in particular ethanol. A stoichiometric or non-stoichiometric amount of solvent is bound by non-covalent intermolecular forces. When the solvent is water, the "solvate" is a "hydrate." It is understood, that a "pharmaceutically acceptable salts" can in addition optionally contain a "solvate".

The term "polymorph" as used herein refers to a crystalline form of a compound or a salt, or a solvate, in particular hydrate, thereof or a solvate, in particular a hydrate, of a salt thereof, in a particular crystal packing arrangement. All polymorphs have the same elemental composition.

The term "crystalline" as used herein, refers to a solid-state form which consists of orderly arrangement of structural units. Different crystalline forms of the same compound, or a salt, or a solvate, in particular a hydrate, thereof or a solvate, in particular a hydrate, of a salt thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability, and solubility.

"A week" preferably refers to a period of time of or about 5, about 6 or about 7 days. It may be about 5-8 days.

"A month" preferably refers to a period of time of or about 28, about 29, about 30 or about 31 days. It may be about 26-33 days.

"Treatment" as used herein preferably comprises the sequential succession of an "induction treatment" and then the "maintenance treatment". Typically, a treatment according to the invention comprises an induction treatment for about one week in which the half daily dose is administered, followed by maintenance treatment in which the full daily dose of about 10 mg to 45 mg vidofludimus and/or a pharmaceutically acceptable salt and/or a solvate, in particular a hydrate, thereof and/or a solvate, in particular a hydrate, of a pharmaceutically acceptable salt thereof is administered.

"Daily dose" preferably refers to the total dose of vidofludimus or a pharmaceutically acceptable salt or a solvate, in particular a hydrate, thereof or a solvate, in particular a hydrate, of a pharmaceutically acceptable salt thereof orally administered to the patient each day of administration. The daily dose can be reached through a single or several administrations per day, such as for example once a day, twice a day or three times a day. Preferably, it is reached or achieved by single administration per day, preferably consisting of one or more tablets or capsules, preferably tablets or capsules as described herein.

Patients suffering from MS can be defined for example as having clinically definite or laboratory-definite MS according to Schumacher or Poser criteria (Schumacher et al., Ann. NY Acad. Sci. 1965; 122:552; Poser et al., Ann. Neurol. 1983; 13:227).

"Relapses" preferably involve neurologic problems that occur over a short period, typically days but sometimes as short as hours or even minutes. These attacks most often involve motor, sensory, visual or coordination problems early in the disease. Later, bladder, bowel, sexual and cognitive problems may be shown. Sometimes the attack onset occurs over several weeks. Typical MS relapse involves a period of worsening, with development of neurological deficits, then a plateau, in which the patient is not getting any better but also not getting any worse followed by a recovery period. Recovery usually begins within a few weeks.

The "annualized relapse rate" is the average number of relapses a group of patients in a clinical study have in one year. See e.g. Multiple Sclerosis Coalition. The Use Of Disease—Modifying Therapies In Multiple Sclerosis: Principles and Current Evidence Summary. Available at http://www.nationalmssociety.org/getmedia/1e64b96c-9e55-400e-9a64-0cdf5e2d60fe/summaryDMTpaper_-final.

The "confirmed disease progression" measures the increase in a patient's EDSS score that is sustained over a pre-determined time period, which means a patient's physical disability has increased as described in e.g. Wiendl et al. Drugs. 2015; 75:947.

The term "brain atrophy" describes one of the most destructive consequences of MS. Brain atrophy can be seen in the earliest stages of MS and may lead to irreversible neurological and cognitive impairments. Progressive loss of brain tissue bulk can be detected in vivo in a sensitive and reproducible manner by MRI. See e.g. Bermel et al. Lancet Neurol. 2006; 5:158.

"Efficacy" of a treatment according to the invention can be preferably measured based on changes in the course of disease in response to a use according to the invention. For example, treatment of MS efficacy can be measured by the frequency of relapses in rrMS and the presence or absence of new lesions in the CNS as detected using methods such as MRI technique (Miller et al., Neurology 1996; 47(Suppl 4):S217; Evans et al., Ann. Neurology 1997; 41:125).

Preferably, the observation of the reduction and/or suppression of MRI T1 gadolinium-enhanced lesions (thought to represent areas of active inflammation) gives a primary efficacy variable. Shows active lesions that appear bright white on an MRI scan after administration of an intravenous imaging contrast agent (gadolinium). Secondary efficacy variables preferably include MRI T1 enhanced brain lesion volume, MRI T1 enhanced lesion number, MRI T2 lesion volume (thought to represent total disease burden, i.e. demyelination, gliosis, inflammation and axon loss), MRI T1 enhanced hypointense lesion volume (thought to represent primarily demyelination and axon loss), time-to-progression of MS, frequency and severity of exacerbations and time-to-exacerbation, Expanded Disability Status Scale score and Scripps Neurologic Rating Scale (SNRS) score (Sipe et al., Neurology 1984; 34:1368). Methods of early and accurate diagnosis of multiple sclerosis and of following the disease progression are described in Mattson, Expert Rev. Neurother. 2002; 2:319.

Degree of disability of MS patients can be for example measured by Kurtzke Expanded Disability Status Scale (EDSS) score (Kurtzke, Neurology 1983; 33:1444). Typically, a decrease in EDSS score corresponds to an improvement in the disease and conversely, an increase in EDSS score corresponds to a worsening of the disease.

As used herein, the term "effective amount" includes a dosage sufficient to produce a desired result with respect to the indicated disorder, condition, or mental state. The desired result may comprise a subjective or objective improvement in the recipient of the dosage.

As used herein, the term "administering" includes activities associated with providing a patient an amount of vidofludimus and/or a pharmaceutically acceptable salt and/or a solvate, in particular a hydrate, thereof and/or a solvate, in particular a hydrate, of a pharmaceutically acceptable salt thereof. Administering includes providing unit dosages of compositions set forth herein to a patient in need thereof. Administering includes providing effective amounts of compounds, e.g. vidofludimus and/or a pharmaceutically acceptable salt and/or a solvate, in particular a hydrate, thereof and/or a solvate, in particular a hydrate, of a pharmaceutically acceptable salt thereof, for a specified period of time, e.g. for about 6, 9, 12, 15 or more months, or about 1, 2, 3, 4, 5 or more years.

As used herein, the term "administered as adjunct therapy" includes sequential or simultaneous administration of two or more structurally different compounds. For example, two or more structurally different pharmaceutically active compounds can be co-administered by administering a pharmaceutical composition adapted for oral administration that contains two or more structurally different active pharmaceutically active compounds. As another example, two or more structurally different compounds can be co-administered by administering one compound and then administering the other compound. In some instances, the co-administered compounds are administered by the same route. In other instances, the co-administered compounds are administered via different routes. For example, one compound can be administered orally, and the other compound can be administered, e.g. sequentially or simultaneously, via intravenous or intraperitoneal injection.

The term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of plus/minus 15% and especially of plus/minus 10%.

Compositions

Compositions may further comprise one or more pharmaceutically acceptable additional ingredient(s) such as alum, stabilizers, antimicrobial agents, buffers, coloring agents, flavoring agents, adjuvants, and the like.

Compositions may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maize starch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

Compositions may also be liquid formulations including, but not limited to, aqueous or oily suspensions, solutions, emulsions, syrups, and elixirs. The compositions may also be formulated as a dry product for constitution with water or other suitable vehicle before use, such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminium stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Combination

Preferably, vidofludimus and/or a pharmaceutically acceptable salt and/or a solvate, in particular a hydrate, thereof and/or a solvate, in particular a hydrate, of a pharmaceutically acceptable salt thereof can be administered alone or in combination with interferon beta 1-a, interferon beta 1-b, glatiramer acetate, mitoxantrone, ocrelizumab, natalizumab, alemtuzumab, dialkyl fumarate, laquinimod, siponimod or fingolimod, prophylactically or therapeutically to an individual prior to, simultaneously or sequentially with other therapeutic regimens or agents (e.g. multiple drug regimens), in a therapeutically effective amount, especially therapeutic agents for the treatment of multiple sclerosis. Active agents that are administered simultaneously with other therapeutic agents can be administered in the same or different compositions and in the same or different routes of administration.

In one embodiment, the subject-matter of the present invention refers to a composition, comprising vidofludimus and/or a pharmaceutically acceptable salt and/or a solvate, in particular a hydrate, thereof and/or a solvate, in particular a hydrate, of a pharmaceutically acceptable salt thereof and at least one therapeutic agent.

In one embodiment, the subject-matter of the present invention refers to a composition, comprising vidofludimus and/or a pharmaceutically acceptable salt and/or a solvate, in particular a hydrate, thereof and/or a solvate, in particular a hydrate, of a pharmaceutically acceptable salt thereof and at least one immunomodulating agent.

In one embodiment, the subject-matter of the present invention refers to a composition, comprising vidofludimus and/or a pharmaceutically acceptable salt and/or a solvate, in particular a hydrate, thereof and/or a solvate, in particular a hydrate, of a pharmaceutically acceptable salt thereof and at least one agent selected from the group consisting of interferon beta 1-a, interferon beta 1-b, glatiramer acetate, mitoxantrone, ocrelizumab, natalizumab, alemtuzumab, dialkyl fumarate, laquinimod, siponimod and fingolimod.

In one embodiment, the subject-matter of the present invention refers to a kit, comprising vidofludimus and/or a pharmaceutically acceptable salt and/or a solvate, in particular a hydrate, thereof and/or a solvate, in particular a hydrate, of a pharmaceutically acceptable salt thereof and at least one therapeutic agent.

In one embodiment, the subject-matter of the present invention refers to a kit, comprising vidofludimus and/or a pharmaceutically acceptable salt and/or a solvate, in particular a hydrate, thereof and/or a solvate, in particular a hydrate, of a pharmaceutically acceptable salt thereof and at least one immunomodulating agent.

In one embodiment, the subject-matter of the present invention refers to a kit, comprising vidofludimus and/or a pharmaceutically acceptable salt and/or a solvate, in particular a hydrate, thereof and/or a solvate, in particular a hydrate, of a pharmaceutically acceptable salt thereof and at least one further agent selected from the group consisting of interferon beta 1-a, interferon beta 1-b, glatiramer acetate, mitoxantrone, ocrelizumab, natalizumab, alemtuzumab, dialkyl fumarate, laquinimod, siponimod and fingolimod.

The term "interferon-beta" (IFN-$\beta$), as used herein, is preferably intended to include fibroblast interferon in particular of human origin, as obtained by isolation from biological fluids or as obtained by DNA recombinant techniques from prokaryotic or eukaryotic host cells, as well as its salts, functional derivatives, variants, analogues and active fragments. IFN-$\beta$ preferably suitable for use in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogues, and active fragments thereof.

Rebif® (recombinant human interferon-$\beta$) is one of the latest developments in interferon therapy for multiple sclerosis (MS) and is believed to represent a significant advance in MS therapy Rebif® is interferon (IFN)-beta 1a, produced from mammalian cell lines. It was established that interferon beta-1a given subcutaneously three times per week is efficacious in the treatment of rrMS. Interferon beta-1a can have a positive effect on the long-term course of MS by reducing number and severity of relapses and reducing the burden of the disease and disease activity as measured by MRI.

If applicable in accordance with the present invention, in case where IFN is recombinant interferon beta 1-b produced in *E. coli*, commercially available under the trademark Betaseron®, it may preferably be administered sub-cutaneously every second day at a dosage of about of 250 to 300 µg or 8 MIU to 9.6 MIU per person.

If applicable in accordance with the present invention, in case where IFN is recombinant interferon beta 1-a, produced in Chinese Hamster Ovary cells (CHO cells), commercially available under the trademark Avonex®, it may preferably be administered intra-muscularly once a week at a dosage of about of 30 µg to 33 µg or 6 MIU to 6.6 MIU per person.

In accordance with the present invention, when IFN is recombinant interferon beta 1-a, produced in Chinese Hamster Ovary cells (CHO cells), commercially available under the trademark Rebif®, it may preferably be administered sub-cutaneously three times a week (TIW) at a dosage of 22 to 44 µg or 6 MIU to 12 MIU per person.

Patients

Preferably, patients according to the invention are patients suffering from relapsing-remitting MS (rrMS) or progressive MS (pMS).

rrMS is characterized by unpredictable relapses followed by periods of months to years of relative quiet (remission) with no new signs of disease activity. Deficits that occur during attacks may either resolve or leave problems, the latter in about 40% of attacks and being more common the longer a person has had the disease. This describes the initial course of 80% of individuals with MS.

Patients according to the invention are patients suffering from pMS can be split up in primary progressive Multiple Sclerosis (ppMS), secondary progressive Multiple Sclerosis (spMS) and early secondary progressive Multiple Sclerosis (espMS).

Preferably, according to this invention, patients are selected from human males or females between 10 and 70 of age, more preferably between 18 and 65 years of age, even more preferably 18 and 55 years of age, and especially 18 and 51 years of age. Since female patients are in the vast majority and often have a higher disease burden, the treatment of female patients is preferred.

EXAMPLES

Example 1: Randomized, Double-Blind, Placebo-Controlled, Multicenter Phase 2 Trial Assessing the Effect of Vidofludimus Calcium on Disease Activity, as Measured by Magnetic Resonance Imaging (MRI), as Well as Safety and Tolerability in Patients with Relapsing-Remitting Multiple Sclerosis (rrMS) (EMPhASIS)—Cohort 1

EMPhASIS is a clinical trial registered with ClinicalTrials.gov (NCT03846219) and EudraCT (2018-001896-19).

Study design and participants: EMPhASIS is a study performed in subjects with MS to assess the efficacy, safety, and tolerability of vidofludimus calcium 30 mg or 45 mg over placebo-controlled in a double-blind design and enrolled 210 patients 18-55 years with relapsing-remitting multiple sclerosis, an Expanded Disability Status Scale score of 0-4 and evidence of disease activity in the past 12-24 months from 38 centers in Europe. Eligible patients were randomly assigned in a 1:1:1 ratio by an interactive web response system to receive once-daily vidofludimus calcium (30 mg or 45 mg) or placebo over a 24 week period.

Procedures: Participants took vidofludimus calcium (30 mg or 45 mg) or placebo once daily in the morning in a fasted state (before breakfast) for 24 weeks. To minimize the risk of changes to uric acid during the first seven days of dosing (induction phase), the assigned dose (containing vidofludimus calcium 15 mg, vidofludimus calcium 22.5 mg or placebo) was taken days 0-6 and then the full dose thereafter (maintenance phase).

Participants underwent standardized brain MRI scans at baseline and every 6 weeks after the first day of dosing until week 24. MRI scans were centrally analyzed by a blinded and independent MRI center. Key clinical assessments included Expanded Disability Status Scale (EDSS) score (assessed at baseline, days 0 and 6, and weeks 6, 12, 18 and 24) and the Treatment Satisfaction Questionnaire for Medication (assessed at baseline, week 6 and week 24), which were likewise done at any unscheduled visit due to a suspected relapse. In the case of suspected or protocol-defined confirmed relapse, corticosteroid treatment was provided at the discretion of the investigator. Pharmacokinetic and pharmacodynamic measurements were also collected.

Adverse events were assessed at screening, baseline, day 7, and weeks 6, 12, 18, and 24 and all unscheduled clinic visits. Routine clinical chemistries, haematology, liver function tests, and urinalysis were collected at baseline, day 7, and weeks 6, 12, 18, and 24. Vital signs and electrocardiography were conducted at screening and regularly scheduled intervals. Adverse events of special interest included: red blood cells in urine, haematuria, and retroperitoneal colicky pain with suspected or confirmed nephrolithiasis.

Patients fulfilling protocol-defined criteria for liver events were required to discontinue treatment if at least one of the following was met: an alanine aminotransferase (ALT) or aspartate aminotransferase (AST) greater than eight times the upper limit of normal (ULN); ALT or AST greater than five times the ULN for more than two weeks; ALT or AST greater than three times the ULN and total bilirubin great than two times the ULN (or international normalized ratio of greater at 1.5 times the ULN); ALT or AST greater than three times the ULN with appearance of fatigue, nausea, vomiting, right upper quadrant pain or tenderness, fever, rash or eosinophilia; or indirect bilirubin greater than three times the ULN.

Outcomes: The primary endpoint was the difference in the cumulative number of combined unique active (CUA) lesions up to week 24 between vidofludimus calcium 45 mg and placebo in the intention-to-treat population (i.e., weeks 6 to 24). The key secondary was the same outcome between vidofludimus calcium 30 mg and placebo. A sensitivity analysis of the primary endpoint and key secondary endpoint was done in the per-protocol population and the modified intention-to-treat population. In addition, prespecified subgroup analyses of the primary endpoint and key secondary endpoint in the intention-to-treat population were done based on baseline demographics (gender, age, weight, country), MRI characteristics (gadolinium-enhancing lesions strata) and clinical characteristics (EDSS score, duration of disease and relapse history).

The intention-to-treat population was defined as all randomized patients who received at least one dose of placebo or vidofludimus calcium and were analyzed by the groups to which they were randomized. The safety population included all randomized patients who received at least one dose of placebo or vidofludimus calcium and was analyzed by the treatment assigned. The per-protocol population was defined as all randomized patients receiving at least one dose of placebo or vidofludimus calcium and no violations of major protocol criteria during treatment. The modified intention-to-treat population was defined as all randomized patients receiving at least one dose of placebo or vidofludimus calcium and having all MRI scans available for analysis.

Other secondary endpoints included: the difference in the cumulative number of combined unique active lesions up to week 24 between vidofludimus calcium 45 mg and vidofludimus calcium 30 mg; number or cumulative number of gadolinium-enhancing, T1, or T2 lesions up to 24 weeks; annualized relapse rate from baseline until week 24; proportion of relapse-free patients up to week 24; time-to-first relapse; change in EDSS score from baseline; proportion of patients with EDSS score progression; brain atrophy and other MRI endpoints; and safety and tolerability as assessed by the investigators. Annualized relapse rate was defined as the total number of confirmed relapses divided by the real exposure time in years assessed over the time during the double-blind treatment period. EDSS progression was defined as an increase compared to baseline of at least 1.0 point for patients with a baseline EDSS score of 1.0 to 4.0 or of at least 1.5 points for patients with a baseline EDSS score of 0. Vidofludimus calcium trough concentrations (weeks 6 and 24) were used to assess the correlation between pharmacokinetics and MRI-based assessments. The effects of vidofludimus calcium on serum neurofilament (baseline and week 24) were also analyzed.

Statistical analysis: The primary and secondary efficacy endpoints were analyzed using a generalized linear model with a negative binomial distribution and a logarithmic link function. Independent effects included in the model were: treatment group; baseline volume of T2 lesions; MRI field strength; and baseline number of gadolinium-enhancing lesions. The natural log transformation of the time from the first dose to the date of the last MRI assessment was included as an offset term to account for different lengths of treatment. Rate ratios (and corresponding 95% CIs) were derived from the model to compare the cumulative number of combined unique active lesions between groups. Analysis of the key secondary endpoint was conducted hierarchically to the primary endpoint. Both tests were performed at a significance level of 0.1 (one-sided).

All other secondary efficacy analyses were reported using descriptive statistics and were considered exploratory. The mean number or cumulative number of gadolinium-enhancing (Gd+), T1, or T2 lesions were summarized descriptively and analyzed with a generalized linear model as described earlier but adjusted for MRI field strength and baseline number of gadolinium-enhancing lesions only. Annualized relapse rate was compared between treatment groups and between the pooled vidofludimus calcium groups and placebo using a generalized linear model adjusted for baseline number of gadolinium-enhancing lesions, which included the offset term for real exposure time. Time-to-first relapse up to 24 weeks was analyzed using a Cox proportional hazards model, with covariates for treatment group and baseline gadolinium-enhancing lesions strata. The proportion of patients free of relapse was estimated using the Kaplan-Meier method. Statistical analyses were done using SAS version 9.4 (SAS Institute, Cary, NC, USA).

A sample size of 195 patients (65 patients per group) was designed to have 80% power on the primary endpoint assuming a mean rate of cumulative combined unique active lesions after 24 weeks of 4.5 and 8.0 for vidofludimus calcium 45 mg and placebo, respectively. The sample size calculation was based on a one-side test for the ratio of two negative binomial rates assuming a negative binomial dispersion parameter of 1.7, a 25% withdrawal rate and a 10% overall type I error rate. No interim analysis was planned or performed.

Results

Of 284 patients screened, 210 were randomized to receive placebo (n=69), vidofludimus calcium 30 mg (n=72), or vidofludimus calcium 45 mg (n=69), one of whom withdrew consent and was not treated (vidofludimus calcium 30 mg group). Most of the patients who did not meet eligibility criteria were excluded because they received corticosteroids within 30 days of the screening MRI. 209 patients received at least one dose of placebo or vidofludimus calcium and comprised the intention-to-treat population and safety population. 198 (95%) of 209 patients completed the study and completion rates were similar between the placebo (n=64 [93%]), vidofludimus calcium 30 mg (n=69 [97%]), and vidofludimus calcium 45 mg (n=65 [94%]) groups. In total, 11 (5%) of 209 patients discontinued the study treatment prematurely, which consisted of five (7%) patients assigned placebo, two (3%) assigned vidofludimus calcium 30 mg, and four (6%) assigned vidofludimus calcium 45 mg. Five discontinuations where attributable to treatment-emergent adverse events in the placebo (n=3) and vidofludimus calcium (n=2) groups. The per-protocol population consisted of 188 (90%) of 209 patients.

Overall, baseline patient demographics, clinical, and MRI characteristics were comparable between groups although the vidofludimus calcium 30 mg group consisted of slightly less females. 129 (62%) of 209 patients had no prior exposure to disease-modifying therapy.

In the primary analysis is shown in Table 1.

TABLE 1

Cumulative number of combined unique active lesions up to 24 weeks (intention-to-treat population)

| Comparison | Cumulative CUA lesions | Rate ratio | 95% Cl | p-value |
| --- | --- | --- | --- | --- |
| Primary endpoint (45 mg vs placebo) | | | | |
| Placebo (n = 69) | 6.3 (2.8-13.9) | — | — | — |
| Vidofludimus calcium 45 mg (n = 69) | 2.4 (1.1-4.9) | 0.38 | 0.22-0.64 | p = 0.00020 |
| Key secondary endpoint (30 mg vs placebo) | | | | |
| Placebo (n = 69) | 13.2 (6.6-26.4) | — | — | — |
| Vidofludimus calcium 30 mg (n = 71) | 4.0 (2.2-7.2) | 0.30 | 0.17-0.53 | p < 0.0001 |
| Secondary endpoint (45 mg vs 30 mg) | | | | |
| Vidofludimus calcium 45 mg (n = 69) | 4.4 (2.4-8.1) | — | — | — |
| Vidofludimus calcium 30 mg (n = 71) | 4.2 (2.5-7.1) | 0.96 | 0.56-1.63 | nc |

Data are adjusted mean (95% Cl). CUA = combined unique active. nc = not calculated.

Consistent results were observed in a pre-planned sensitivity analysis of the per-protocol population and the modified intention-to-treat population. Prespecified univariate subgroup analyses also found fewer adjusted mean cumulative number of combined unique active lesions up to 24 weeks in either vidofludimus calcium groups as compared to placebo in most subgroups tested, although significance analysis was not conducted because they were exploratory outcomes. No notable difference in the adjusted mean cumulative number of combined unique active lesions up to 24 weeks was observed between vidofludimus calcium 30 mg and 45 mg. Lower adjusted mean cumulative number of combined unique active lesions up to 24 weeks in either vidofludimus calcium groups compared to placebo was evident as early as week 6 and continued through week 24. This observation was similar when assessing the adjusted mean cumulative number of gadolinium-enhancing lesions up to 24 weeks (FIG. 1). The cumulative number of new gadolinium-enhancing lesions at week 24 was 13.0 (95% CI 6.8-24.5) with placebo, 4.5 (95% CI 2.7-7.7) with vidofludimus calcium 30 mg and 4.0 (95% CI 2.1-7.8) with vidofludimus calcium 45 mg. The adjusted mean annualized relapse rate was 0.53 (95% CI 0.32-0.89) with placebo, 0.39 (95% CI 0.22-0.69) with vidofludimus calcium 30 mg and 0.48 (95% CI 0.28-0.82) with vidofludimus calcium 45 mg. The rate ratio between vidofludimus calcium 30 mg vs placebo and vidofludimus calcium 45 mg vs placebo was 0.72 (95% CI 0.34-1.55) and 0.90 (95% CI 0.44-1.86), respectively. The hazard ratio for relapse up to 24 weeks between vidofludimus calcium 30 mg vs placebo and vidofludimus calcium 45 mg vs placebo was 0.58 (95% CI: 0.26-1.29) and 0.78 (95% CI: 0.37-1.59), respectively. Median change in neurofilament light chain in serum from baseline to week 24 was 6.5%, −17.0% and −20.5% for placebo, vidofludimus calcium 30 mg and vidofludimus calcium 45 mg, respectively.

Both doses of vidofludimus calcium were well tolerated. A similar proportion of patients experienced at least one treatment-emergent adverse event in the placebo (44%), vidofludimus calcium 30 mg (45%) and vidofludimus calcium 45 mg (41%) groups, which were predominantly mild or moderate in severity. Alopecia, fatigue, rash, and cystitis were treatment-emergent adverse events that occurred in greater than one percent of vidofludimus calcium-treated patients that were not recorded in placebo-treated patients (1-4%). Serious adverse events were low (0-3%). Three patients experiencing four serious adverse events occurred in the vidofludimus calcium 30 mg (n=2) and the placebo group (n=1) and were considered unrelated to treatment: hydronephrosis and ureterolithiasis (vidofludimus calcium 30 mg), open fracture (vidofludimus calcium 30 mg) and squamous cell carcinoma of the cervix (placebo). The two most common treatment-emergent adverse events, headache and nasopharyngitis, occurred with similar frequency between the placebo and either vidofludimus calcium groups. No remarkable cardiovascular, haematological, infectious or malignancy-related adverse events were noted. Adverse events of special interest occurred in one (1%) patient treated with placebo (haematuria) and one (1%) patient treated with any dose of vidofludimus calcium (ureterolithiasis). Renal treatment-emergent events occurred in one (1%) patient treated with placebo and three (2%) patients treated with any dose of vidofludimus calcium. No marked changes in serum uric acid were apparent in any treatment group over 24 weeks. No deaths occurred during the trial.

Hepatic treatment-emergent adverse events were recorded in three (4%) patients treated with placebo and in six (4%) patients treated with any dose of vidofludimus calcium. Rises in ALT or AST greater than five times the ULN occurred in two (3%) patients with placebo, one (1%) patient with vidofludimus calcium 30 mg and three (4%) patients with vidofludimus calcium 45 mg. Of the five patients who discontinued treatment due to treatment-emergent adverse events, one in the placebo group and two in the vidofludimus calcium 45 mg group met hepatotoxicity stopping rules. One additional patient in the placebo group experienced an ALT increase of greater than eight times the ULN and was discontinued at the investigator's discretion before hepatotoxicity stopping rules were applied. All occurrences were mild or moderate, did not occur with clinically significant increases in bilirubin and resolved following treatment discontinuation.

Discussion: A once-daily oral dose of vidofludimus calcium 30 mg or 45 mg resulted in significantly fewer number of combined unique active MRI lesions up to 24 weeks when compared to placebo. Suppression of MRI lesions was evident as early as week 6 and was consistent through week 24. Other MRI outcomes, including the cumulative number of T1, T2, and gadolinium-enhancing lesions up to 24 weeks were consistent with study's primary findings. Both doses of vidofludimus calcium were well tolerated. The incidence of the two most common treatment-emergent adverse events—nasopharyngitis and headache—were low and similar between vidofludimus calcium- and placebo-treated patients. Moreover, no increased incidence in liver, renal or infection-related treatment-emergent adverse events were observed. No changes in haematologic laboratory values, as measured by neutrophil, lymphocyte, and leukocyte count, were observed with vidofludimus calcium, suggesting negative effects on the broad, peripheral immune cell population did not occur. This observation is consistent with the mechanism of action of vidofludimus calcium and its biological selectivity towards activated T and B cells with high metabolic requirements needed for DHODH-mediated pyrimidine synthesis. No notable differences between vidofludimus calcium 30 mg and 45 mg on MRI outcomes were evident and both doses of vidofludimus calcium had a comparable safety profile. In conclusion, vidofludimus calcium significantly suppressed the development of new MRI lesions and demonstrated a favorable safety and tolerability profile.

Example 2: Randomized, Double-Blind, Placebo-Controlled, Multicenter Phase 2 Trial Assessing the Effect of Vidofludimus Calcium on Disease Activity, as Measured by Magnetic Resonance Imaging (MRI), as Well as Safety and Tolerability in Patients with Relapsing-Remitting Multiple Sclerosis (rrMS) (EMPhASIS)—Cohort 2 with Interim Analysis after 12 Weeks Given the relative equal performance of the two doses in Cohort 1 (see Example 1) and to allow for pharmacodynamic modeling of the dose-response relationship, a lower dose was investigated. The objective of the Cohort 2 sub-trial is to obtain exploratory data on the dose response of IMU-838 by evaluating a lower IMU-838 dose i.e. 10 mg/day to provide additional data for pharmacodynamic modelling. The 10 mg IMU-838 dose was selected since it is more than 50% lower than the lowest effective dose of Cohort 1 (30 mg IMU 838) and avoids undesired overlap in serum trough levels for pharmacodynamic modelling of the pooled Cohort 1 and 2 data. A small placebo arm is included to provide blinding of patients and to relate Cohort 2 treatment effects. Assessments and procedures mostly follow those described for the main treatment period in the Cohort 1 main trial.

Trial objectives and endpoints: The objective of this sub-trial is to obtain more efficacy and safety data of IMU-838 in patients with RRMS and to allow pharmacodynamic modelling of the dose response. The endpoints analyzed in this interim analysis were between-treatment differences in the following MRI parameters: cumulative number of CUA MRI lesions up to Week 12; cumulative number of new Gadolinium enhancing (Gd+) lesions up to Week 12; proportion of patients without CUA MRI lesions until Week 12; and proportion of patients without new Gd+ lesions until Week 12.

Overall trial design and plan: This is a double-blind, placebo-controlled, randomized, parallel-group sub-trial of P2 IMU-838 MS to assess the efficacy and safety of once-daily oral 10 mg/day IMU-838 compared to placebo in patients with RRMS and evidence of active disease. The sub-trial consists of a blinded main treatment period and an open-label, extended treatment period (FIG. 2). Patients were randomized 1:4 to placebo and 10 mg IMU-838 on Day 0.

Efficacy Results a) Cumulative Number of CUA MRI or New Gd+ Lesions Up to Week 12

The mean cumulative number of CUA MRI or Gd+ lesions from Baseline to Week 12 with each treatment is shown in Table 2. Compared with placebo CUA or Gd+ lesions were reduced with IMU-838 at Week 12. The effect increased with increasing dose of IMU-838. Treatment with 10 mg IMU-838 suppressed CUA and Gd+ lesions by 32% and 40%, respectively, whereas a suppression of 68% and 66%, respectively, was observed with 30 mg and of 75% and 74%, respectively, with 45 mg.

treatment to obtain an early assessment of dose-response indicated that 10 mg IMU-838 is effective in suppressing MS-related MRI activity as compared with placebo. Due to the limited number of patients treated with placebo in Cohort 2, data from selected Cohort 1 patients at the same sites used in both cohorts were added to enrich this interim analysis. Comparing selected MRI outcomes at Week 12 of the 10 mg IMU-838 treatment group with the respective data from Cohort 1 patients treated with 30 mg or 45 mg IMU-838, the effect of the 10 mg dose was shown to be less efficacious than the two higher doses. From the totality of data of Cohort 1 and the Week 12 interim analysis of Cohort 2, IMU-838 30 mg should be considered the lowest effective dose in patients with rrMS, although the IMU-838 doses 30 mg and 45 mg were equally effective on efficacy endpoints

TABLE 1

Cumulative number of CUA MRI or new Gd+ lesions up to Week 12 (mFAS C1 and C2)

| Cumulative number of | | Placebo (C1, C2) | | 10 mg IMU-838 (C2) | | 30 mg IMU-838 (C1) | | 45 mg IMU-838 (C1) | |
|---|---|---|---|---|---|---|---|---|---|
| | | Mean | SD | Mean | SD | Mean | SD | Mean | SD |
| CUA lesions | MRI | 4.4 | 12.9 | 3.0 | 4.9 | 1.4 | 2.6 | 1.1 | 1.8 |
| New lesions | Gd+ | 3.5 | 11.0 | 2.0 | 3.8 | 1.2 | 2.4 | 0.9 | 1.7 |

C1/2 = Cohort 1 or 2, CUA = combined unique active, Gd+ = gadolinium enhancing, mFAS = modified full analysis set, MRI = magnetic resonance imaging, SD = standard deviation.

b) Proportion of Patients without CUA MRI or Gd+ Lesions Over 12 Weeks

The percentage of patients without CUA MRI or Gd+ lesions over 12 weeks is summarized in Table 3. 41% and 49% of patients on placebo treatment did not develop CUA and Gd+ lesions, respectively, over 12 weeks, compared with 46% and 51% of patients, respectively, treated with 10 mg IMU-838. Higher percentages of patients without CUA or Gd+ lesions within this period were observed with 30 mg IMU-838 (62% and 66%) and with 45 mg IMU-838 (55% and 61%).

as evaluated in Cohort 1 with no safety signals over placebo for either dose. In conclusion, a daily dose of 30 mg of IMU-838 is preferred for the treatment of rrMS.

Example 3: Change in Serum Neurofilament Light Chain (NfL) from Baseline to Week 24 in rrMS in the EMPhASIS Study Based on pre-clinical and clinical studies and the single and multiple-dose Phase 1 studies with IMU-838, daily doses of IMU-838 of up to 50 mg once daily are considered

TABLE 2

Proportion of patients without CUA MRI or Gd+ lesions over 12 weeks (mFAS 01 and 02)

| Patients without | | Placebo (C1, C2) | | 10 mg IMU-838 (C2) | | 30 mg IMU-838 (C1) | | 45 mg IMU-838 (C1) | |
|---|---|---|---|---|---|---|---|---|---|
| | | % | 95% CI | % | 95% CI | % | 95% CI | % | 95% CI |
| CUA lesions | MRI | 41.4 | 29.8; 53.8 | 45.7 | 30.9; 61.0 | 61.5 | 48.6; 73.3 | 54.5 | 41.8; 66.9 |
| New lesions | Gd+ | 49.3 | 37.2; 61.4 | 51.1 | 36.1; 65.9 | 66.2 | 53.4; 77.4 | 60.6 | 47.8; 72.4 |

C1/2 = Cohort 1 or 2, CI = confidence interval, CUA = combined unique active, Gd+ = gadolinium enhancing, mFAS = modified full analysis set, MRI = imagnetic resonance imaging.

Discussion: In Cohort 1 of the Phase 2 Trial P2-IMU-838-MS, treatment with 30 and 45 mg IMU-838 over 24 weeks significantly reduced the cumulative number of CUA MRI lesions as compared with placebo (Example 1). Apparent differences between the 2 treatments and a clear dose response were not found. To obtain further data on the dose response, this sub-trial (Cohort 2) was initiated to investigate the efficacy of IMU-838 at a lower dose (10 mg) versus placebo. An interim analysis performed after 12 weeks of safe. The results of a Phase 2 study (see Example 1 and 2) demonstrated that 30 mg and 45 mg doses of IMU-838 are highly effective in patients with rrMS after 24-weeks of treatment with suppression of MRI activity by 70% for the 30 mg dose. Results also showed a favorable safety profile of IMU-838 at these doses. There was a greater decrease in serum neurofilament light chain (NfL) at 45 mg dose and this provides evidence of greater potential of neuroprotective activity for IMU-838 with increasing doses (FIG. 3A).

A post-hoc analysis from EMPhASIS study (see Example 1 and 2) in the non-relapse active subgroup of rrMS patients was conducted. The mean EDSS in this subgroup of patients without any relapses during the study period has shown that a higher dose of 45 mg IMU-838 may have advantages over the 30 mg dose of IMU 838 regarding unconfirmed EDSS worsening (FIG. 3B). Change in mean EDSS from baseline to Week 24 in a non-relapse active subgroup of rrMS patients (patients without relapse between baseline and Week 24). Based on these data and the safety profile of 45 mg IMU-838 in the EMPhASIS study, the 45 mg dose of IMU-838 is the more appropriate dose for the pMS population.

Example 4: Multicenter, Randomized, Double-Blind, Placebo-Controlled Study to Evaluate Efficacy, Safety and Tolerability of IMU-838 in Patients with Progressive Multiple Sclerosis (pMS)

Name of Investigational Product: Vidofludimus calcium (IMU-838)

Primary Objective: To evaluate the efficacy of IMU-838 versus placebo as measured by quantitative magnetic resonance imaging (MRI) analysis for whole-brain atrophy in progressive multiple sclerosis (PMS) patients with the Structural Image Evaluation using Normalization of Atrophy (SIENA) method. Endpoint: Annualized rate of percent brain volume change (PBVC).

1. Key Secondary Objectives: To evaluate the efficacy of IMU-838 versus placebo as measured by quantitative MRI analysis for whole brain atrophy in PMS patients with the Structural Image Evaluation using the Brain Parenchymal Fraction (BPF) method. Endpoint: Annualized rate of BPF.

2. Key Secondary Objectives: To evaluate the efficacy of IMU-838 compared to placebo in terms of disability worsening. Endpoint: Time to 24-week confirmed disability progression (24wCDP) based on Expanded disability status scale (EDSS).

Study Duration: Approximately 10 years (124 months): Approximately 2 years of double blinded phase and approximately 8 years of open label extension phase (FIG. 4).

Administration: Patients will take 22.5 mg tablet once daily in the morning from D1 until D6 and 45 mg tablet once daily in the morning from D7 until the EoMT (in case the patient not entering the OLE period) or until the EoT (in case the patient is enrolled in the OLE period). Tablets will be taken once daily in the morning in the fasted state (no food after midnight, unrestricted intake of water is always allowed) and taken with a glass of water approximately 15 minutes to 1 hour before breakfast.

Example 5: Content of Different Doses of Vidofludimus

As described above, vidofludimus, in both its free acid form and its calcium salt formulation (vidofludimus calcium), has undergone clinical trials for a variety of immune-related indications. Both formulations depend on the same active substance (vidofludimus) in vivo, and thus the two formulations share the same mechanism of action, pharmacology and toxicology. IMU-838 is the "Polymorph A" of the dihydrate of 1-cyclopentene-1-carboxylic acid, 2-(((3-fluoro-3'-methoxy(1,1'-biphenyl)-4-yl)amino)carbonyl)-, calcium salt (2:1), characterized by an X-ray powder diffraction pattern having characteristic peaks at 2 theta)(±0.2° of 5.91°, 9.64°, 16.78°, 17.81°, 19.81° and 25.41°. The preparation of this "Polymorph A" is described in WO 2019/175396, which is incorporated herein by this reference.

In the following Table 4 the amount (in mg) of active moiety of the compound is converted into μmol.

TABLE 4

| mg IMU-838 | μmol IMU-838 | mg vidofludimus (free acid) |
|---|---|---|
| 45 | 115 | 41 |
| 30 | 76.5 | 27 |
| 10 | 25.5 | 9.1 |

[a] Could be interrupted/extended, if the baseline MRI had to be repeated due to poor quality (was to be done as soon as possible). If results of the central MRI assessment were not available in time for randomization, the screening period could be extended by up to 7 days, if needed.

[b] 30 mg/day IMU-838 is recommended. However, based on discussion between investigator and patient 45 mg/day IMU 838/day may also be used. Switching between open-label doses will be allowed.

[c] The extended treatment period will be terminated for patients in the Cohort 2 sub-trial, at the day the last patient of the Cohort 1 main trial has completed, prematurely or as scheduled, the extended treatment period.

BL=baseline, D=day, EoMT=end-of-main treatment, EoS=end-of-study, EoT=end-of-treatment, exam=examination, FAMT=final analysis of main treatment period, IA=interim analysis, MRI=magnetic resonance imaging, MT=main treatment, R=randomization, Scr.=screening, W=Week.

FIG. 3A: Change in serum neurofilament light chain from baseline to Week 24 in rrMS (EMPhASIS study).

Figure 1:
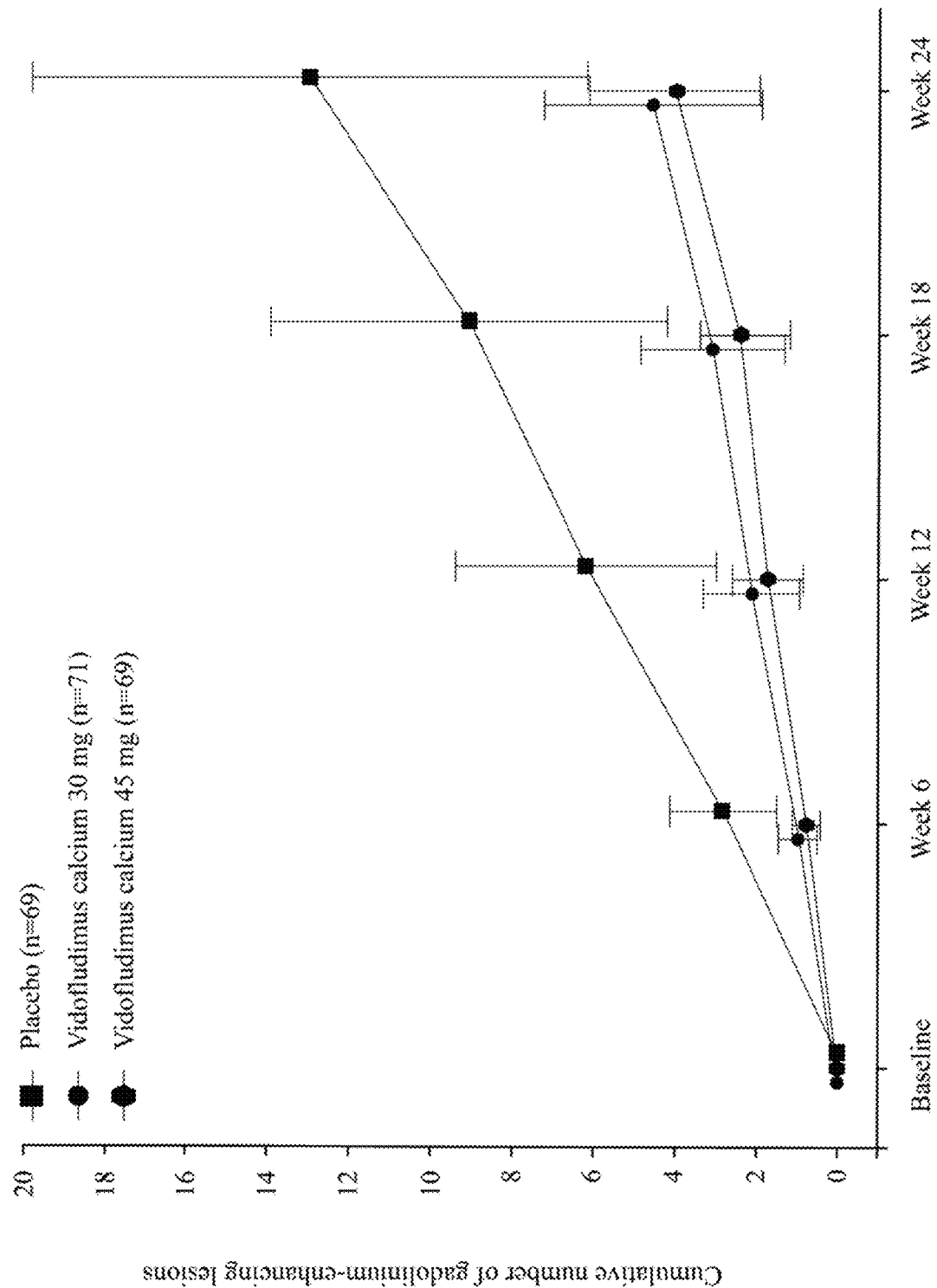
FIG. 1: Cumulative number of gadolinium-enhancing lesions from baseline to Week 24 (intention-to-treat population) from Example 1. Data are presented as adjusted mean with the upper and lower limits of the 95% CIs. Estimates were adjusted for baseline volume of T2 lesions, MRI field strength (1.5 or 3.0 Tesla) and baseline number of gadolinium-enhancing lesions (0 or ≥1) using a generalized linear model with a negative binomial distribution and a logarithmic link function.
Figure 2:
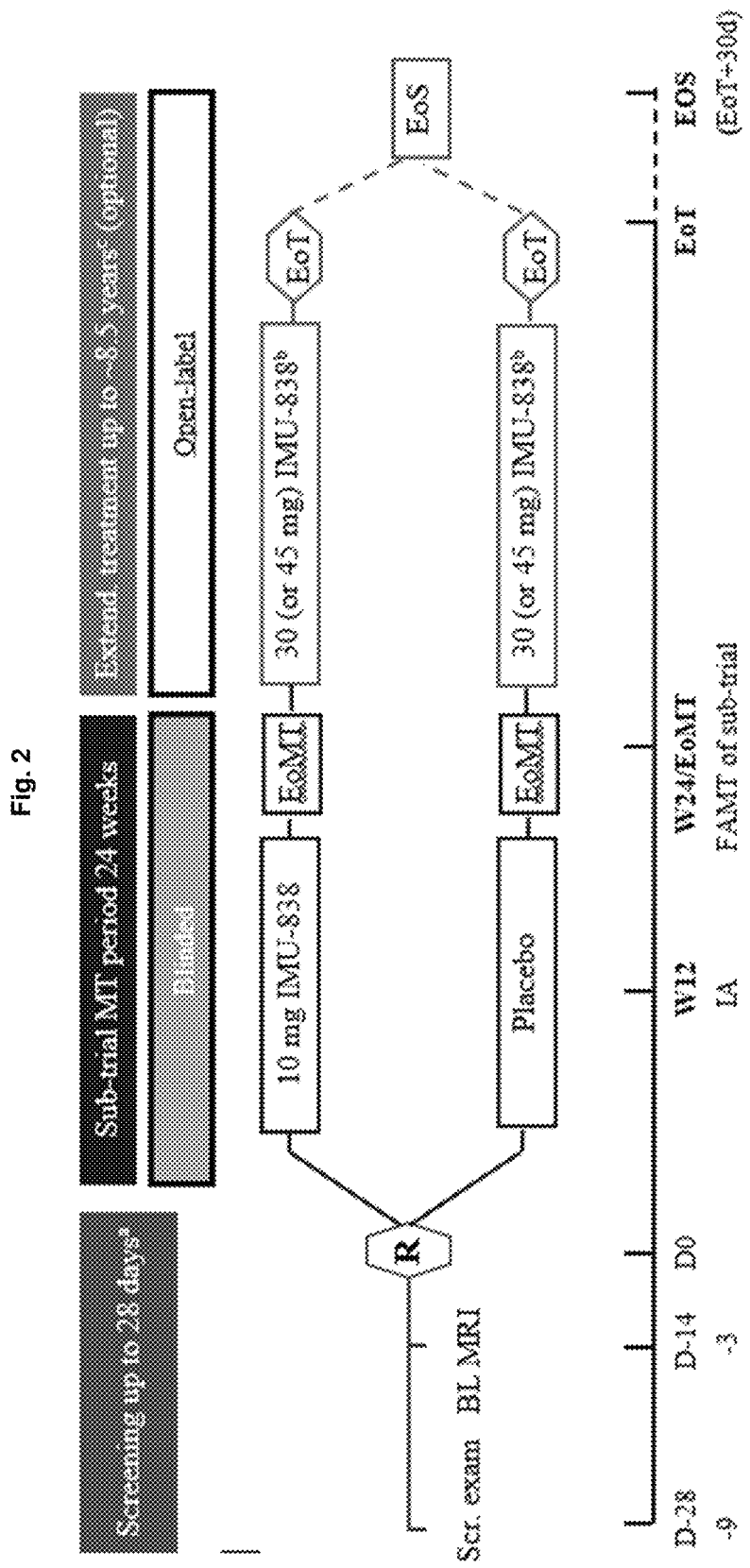
FIG. 2: Trial flow chart—Cohort 2 sub-trial of Example 2
Figure 3B:
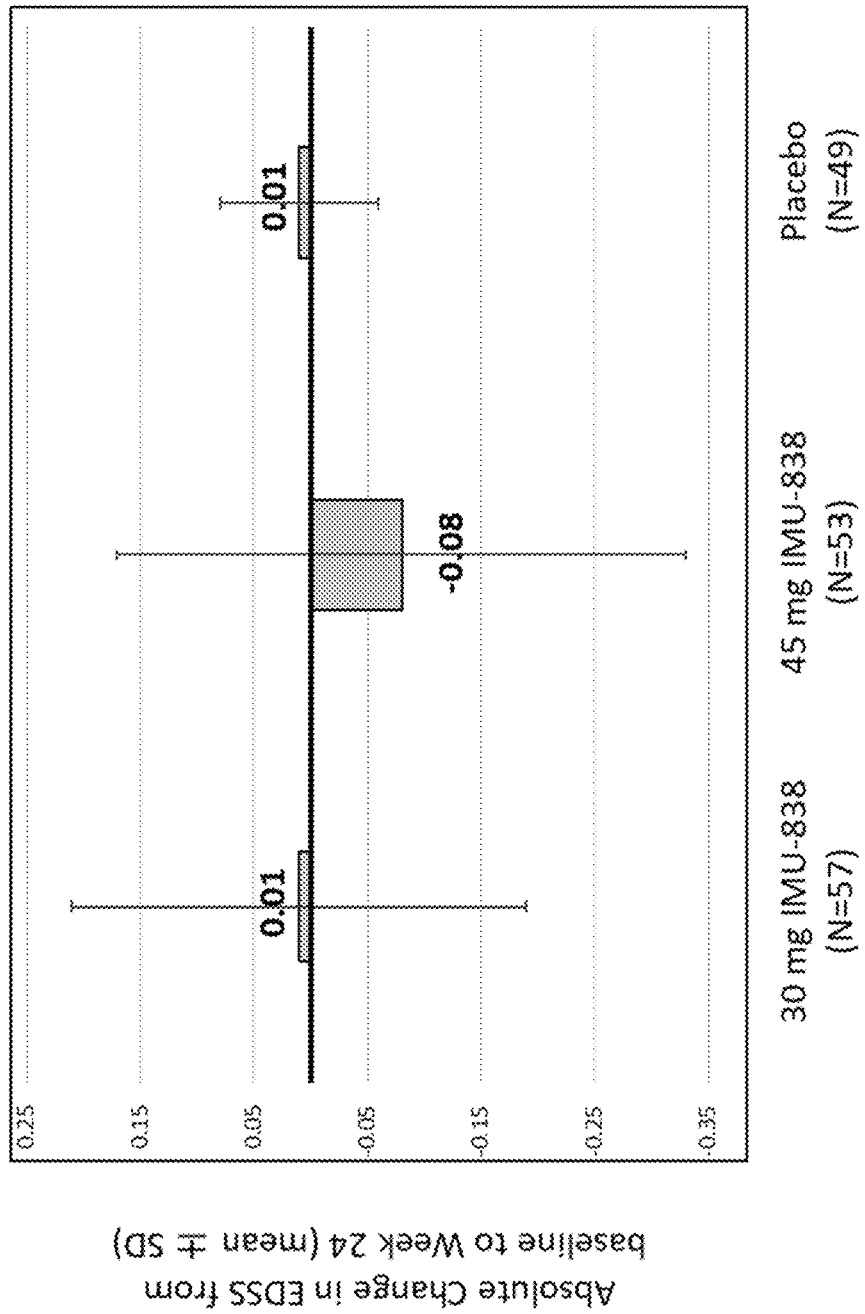

FIG. 3B: Change in mean EDSS from baseline to Week 24 in rrMS (EMPhASIS study).

Figure 4:
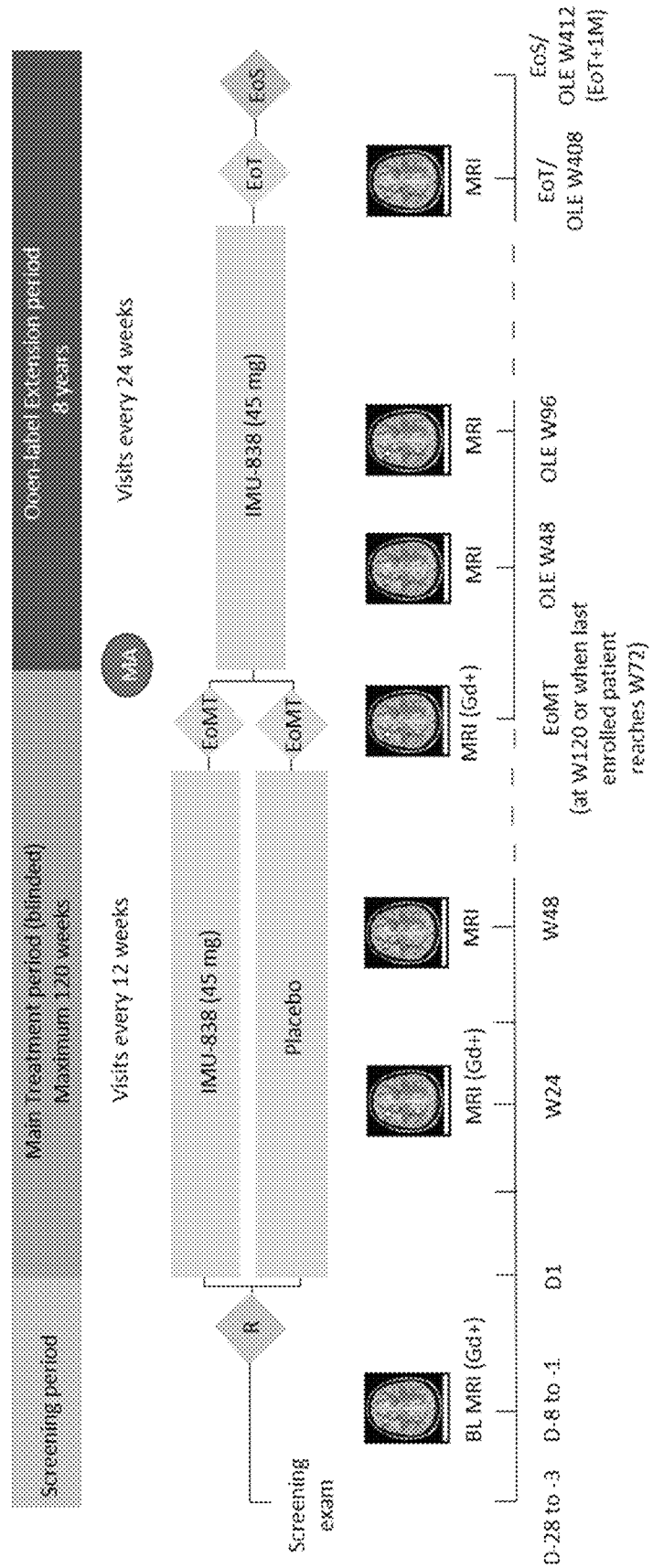

FIG. 4: Trial flow chart of clinicals study of Example 4

BL=baseline, D=day, EoMT=end-of-main treatment, EoS=end-of-study, EoT=end-of-treatment, Gd+=with Gadolinium contrast, M=month, MA=main analysis, MRI=magnetic resonance imaging, OLE=open-label expansion, W=Week.

The invention claimed is:

1. A method of treating a human patient afflicted with relapsing-remitting multiple sclerosis, the method comprising orally administering to the human patient at least one compound chosen from 2-({3-fluoro-3'-methoxy-[1,1'-biphenyl]-4-yl}carbamoyl)cyclopent-1-ene-1-carboxylic acid or a pharmaceutically acceptable salt or a solvate thereof, at a daily dose of about 10 mg to 45 mg of the at least one compound so as to alleviate a symptom of or a condition associated with relapsing-remitting multiple sclerosis, thereby treating the human patient.

2. The method of claim 1, wherein the administration of at least one compound is effective to reduce relapse rate, reduce rate of confirmed relapses requiring hospitalization and/or IV steroids, reduce the accumulation of disability, reduce or inhibit progression of the level of fatigue, improve or inhibit deterioration of the functional status, improve or inhibit deterioration of the general health, reduce MRI-monitored disease activity, decrease the hazard ratio for relapse-free survival or reduce cognitive impairment in the human patient.

3. The method of claim 2, wherein the administration of at least one compound is effective to decrease the hazard ratio for time to confirmed relapse in the human patient.

4. The method of claim 2, wherein the administration of at least one compound is effective to reduce the annualized relapse rate in the human patient.

5. The method of claim 4, wherein the annualized relapse rate is reduced by at least 25%.

6. The method of claim 2, wherein the administration of at least one compound is effective to improve or inhibit deterioration of the general health in the human patient.

7. The method of claim 1, wherein the at least one compound is administered as monotherapy for relapsing-remitting multiple sclerosis.

8. The method of claim 1, wherein the at least one compound is administered as adjunct therapy with another multiple sclerosis treatment.

9. The method of claim 8, wherein the other multiple sclerosis treatment is administration of interferon beta 1-a, interferon beta 1-b, glatiramer acetate, mitoxantrone, ocrelizumab, natalizumab, alemtuzumab, dialkyl fumarate, laquinimod, siponimod or fingolimod.

10. A method for treating a human subject afflicted with relapsing-remitting multiple sclerosis by providing neuroprotection to the human subject comprising orally administering to the human subject a daily dose of about 10 mg to 45 mg at least one compound chosen from 2-({3-fluoro-3'-methoxy-[1,1'-biphenyl]-4-yl}carbamoyl)cyclopent-1-ene-1-carboxylic acid or a pharmaceutically acceptable salt or a solvate thereof to thereby treat the human subject by providing neuroprotection to the human subject.

11. A method of claim 10, the method comprising orally administering to the patient the at least one compound at a daily dose of about 10 mg to 45 mg to thereby treat the human patient by increasing the time to confirmed disease progression, decreasing the hazard ratio for time to confirmed relapse, increasing the time to confirmed relapse or reducing brain atrophy in the human patient.

12. The method of claim 11, wherein the administration of the at least one compound is effective to decrease the hazard ratio for time to confirmed relapse in the human patient.

13. The method of claim 11, wherein the at least one compound is administered as monotherapy for relapsing-remitting multiple sclerosis.

14. The method of claim 1, wherein the at least one compound is administered in the form of a calcium salt dihydrate with the following structure:

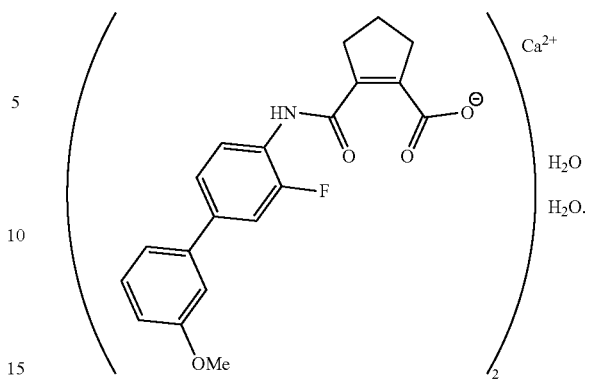

15. The method of claim 1 comprising orally administering to the patient the at least one compound in the form of a tablet or a capsule.

16. The method of claim 1, comprising orally administering the at least one compound, wherein the at least one compound is a calcium salt dihydrate with the following structure:

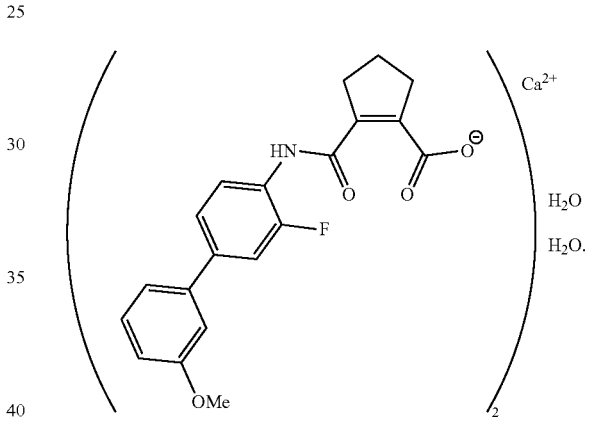

as "Polymorph A" at a daily dose of about 30 mg in the form of a tablet or a capsule.

17. The method of claim 1, comprising orally administering the at least one compound, wherein the at least one compound is a calcium salt dihydrate with the following structure:

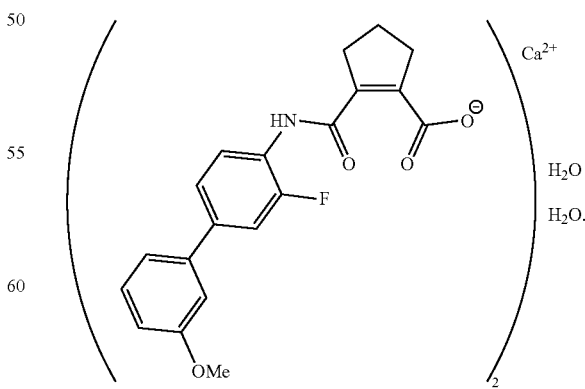

as "Polymorph A" at a daily dose of about 45 mg in the form of a tablet or a capsule.

18. The method of claim 1, wherein the daily dose is calculated based on the weight of 2-({3-fluoro-3'-methoxy-[1,1'-biphenyl]-4-yl}carbamoyl)cyclopent-1-ene-1-carboxylic acid.

* * * * *